US009820631B2

(12) United States Patent
Yasunaga

(10) Patent No.: US 9,820,631 B2
(45) Date of Patent: Nov. 21, 2017

(54) ENDOSCOPE

(71) Applicant: OLYMPUS CORPORATION, Tokyo (JP)

(72) Inventor: Koji Yasunaga, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/218,118

(22) Filed: Jul. 25, 2016

(65) Prior Publication Data

US 2016/0331212 A1    Nov. 17, 2016

Related U.S. Application Data

(63) Continuation of application No. PCT/JP2015/056318, filed on Mar. 4, 2015.

(30) Foreign Application Priority Data

Sep. 2, 2014 (JP) ................................. 2014-178309

(51) Int. Cl.
*A61B 1/00* (2006.01)
*A61B 1/04* (2006.01)
(Continued)

(52) U.S. Cl.
CPC ...... *A61B 1/00096* (2013.01); *A61B 1/00018* (2013.01); *A61B 1/00039* (2013.01);
(Continued)

(58) Field of Classification Search
CPC ... A61B 1/00096; A61B 1/04; A61B 1/00018; A61B 1/00163; A61B 1/00045;
(Continued)

(56) References Cited

U.S. PATENT DOCUMENTS 6,371,909 B1    4/2002 Hoeg et al.
2001/0018553 A1  8/2001 Krattiger et al.
(Continued)

FOREIGN PATENT DOCUMENTS

EP    1166710 A2    1/2002
JP    H06-237881 A    8/1994
(Continued)

OTHER PUBLICATIONS

International Search Report dated Jun. 2, 2015 issued in PCT/JP2015/056318.
Japanese Office Action dated Feb. 2, 2016 issued in JP 2015-548103.

*Primary Examiner* — Timothy J Neal
(74) *Attorney, Agent, or Firm* — Scully, Scott, Murphy & Presser, P.C.

(57) ABSTRACT

An endoscope includes: an operation portion provided continuously with a proximal end of a rigid insertion portion having a longitudinal axis; an optical element disposed at a distal end part of the insertion portion so as to be rotationally movable around a first shaft perpendicular to the longitudinal axis and a second shaft parallel to the longitudinal axis; a single operation member disposed at the operation portion and swingable forward, backward, leftward, and rightward around a third shaft and a fourth shaft perpendicular to each other; a first transmission member that transmits a rotational force around the first shaft to the optical element by a tilting operation of the operation member around the third shaft; and a second transmission member that transmits a rotational force around the second shaft to the optical element by a tilting operation of the operation member around the fourth shaft.

9 Claims, 21 Drawing Sheets

(51) Int. Cl.
  *G02B 23/24* (2006.01)
  *H04N 5/225* (2006.01)
(52) U.S. Cl.
  CPC ...... *A61B 1/00045* (2013.01); *A61B 1/00163* (2013.01); *A61B 1/00183* (2013.01); *A61B 1/04* (2013.01); *G02B 23/2423* (2013.01); *G02B 23/2476* (2013.01); *H04N 5/2254* (2013.01); *H04N 5/2256* (2013.01); *H04N 2005/2255* (2013.01)
(58) Field of Classification Search
  CPC ............ G02B 23/2423; G02B 23/2476; H04N 5/2256; H04N 5/2254; H04N 5/2255
  See application file for complete search history.

(56) References Cited

U.S. PATENT DOCUMENTS

| | | |
|---|---|---|
| 2002/0022767 A1 | 2/2002 | Dohi et al. |
| 2010/0030031 A1 | 2/2010 | Goldfarb et al. |
| 2014/0249369 A1 | 9/2014 | Hanabusa |

FOREIGN PATENT DOCUMENTS

| | | |
|---|---|---|
| JP | 2002-000550 A | 1/2002 |
| JP | 2010-029658 A | 2/2010 |
| JP | 2011-529724 A | 12/2011 |
| JP | 2012-075777 A | 4/2012 |
| WO | WO 00/11999 A1 | 3/2000 |
| WO | WO 2010/014421 A1 | 2/2010 |
| WO | WO 2013051168 A1 | 4/2013 |

ENDOSCOPE

CROSS REFERENCE TO RELATED APPLICATION

This application is a continuation application of PCT/JP2015/056318 filed on Mar. 4, 2015 and claims benefit of Japanese Application No. 2014-178309 filed in Japan on Sep. 2, 2014, the entire contents of which are incorporated herein by this reference.

BACKGROUND OF THE INVENTION

1. Field of the Invention

The present invention relates to a variable direction of view endoscope, and more particularly to an endoscope that changes a direction of view by moving an optical element provided at a distal end portion of an insertion portion.

2. Description of the Related Art

Endoscopes for picking up an optical image, which can be introduced from outside to inside of a living body or structure in order to observe a site such as inside of the living body or an inner portion of the structure where observation is difficult, have been used in medical fields or industrial fields, for example.

Endoscopes have a type including a flexible insertion portion used for examination and treatment of digestive tracts, and a type including a rigid insertion portion used for surgical operation.

Specifically, the endoscope having the rigid insertion portion is called a rigid endoscope, a laparoscope, a pyeloureteroscope, or the like, and as disclosed in Japanese Patent Application Laid-Open Publication No. 2010-29658, for example, a swing prism endoscope is known in which an optical axis is swung by swinging to tilt the prism of the optical element provided at the distal end, to allow the view (perspective angle) to be changed.

SUMMARY OF THE INVENTION

An endoscope according to one aspect of the present invention includes: a rigid insertion portion having a longitudinal axis; an operation portion provided continuously with a proximal end of the insertion portion; an optical element disposed at a distal end part of the insertion portion so as to be rotationally movable around a first shaft perpendicular to the longitudinal axis and a second shaft parallel to the longitudinal axis, and configured to change a direction of view upward, downward, leftward, and rightward; a single operation member disposed at the operation portion and configured to be able to swing forward, backward, leftward, and rightward around a third shaft and a fourth shaft which are perpendicular to each other; a first transmission member to which the optical element and the operation member are connected, the first transmission member being configured to transmit a rotational force around the first shaft to the optical element by a tilting operation of the operation member around the third shaft; and a second transmission member including a distal end part at which the optical element is disposed so as to be rotationally movable around the first shaft, and a proximal end part connected to the operation member, the second transmission member being configured to transmit a rotational force around the second shaft to the optical element by a tilting operation of the operation member around the fourth shaft.

DETAILED DESCRIPTION OF THE PREFERRED EMBODIMENTS

Figure 1:
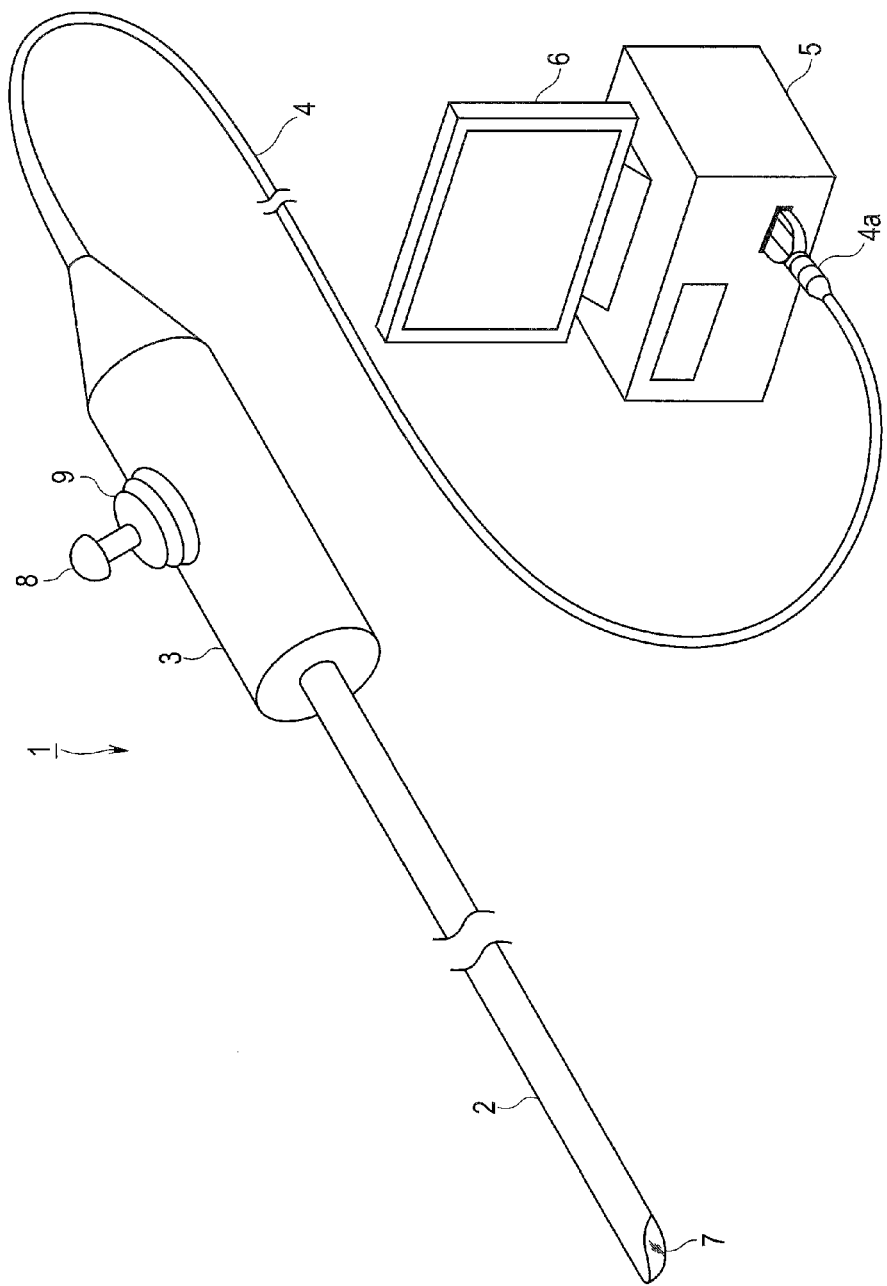
FIG. 1 is a perspective view showing an overall configuration of an endoscope according to a first embodiment.

Hereinafter, preferred embodiments of the present invention will be described with reference to drawings. Note that, in the drawings used in the description below, a different scale size is used for each of the constituent elements in order to allow each of the constituent elements to be illustrated in a recognizable size in the drawings, and the present invention is not limited only to the number, shapes, ratio of the sizes of the constituent elements, and a relative positional relationship among the constituent elements shown in these drawings. In addition, in the description below, the up direction and the down direction viewed facing the paper surface are described as the upper portion and the lower portion of constituent elements in some cases.

First Embodiment

First, an endoscope according to the first embodiment will be described below.

Figure 2:
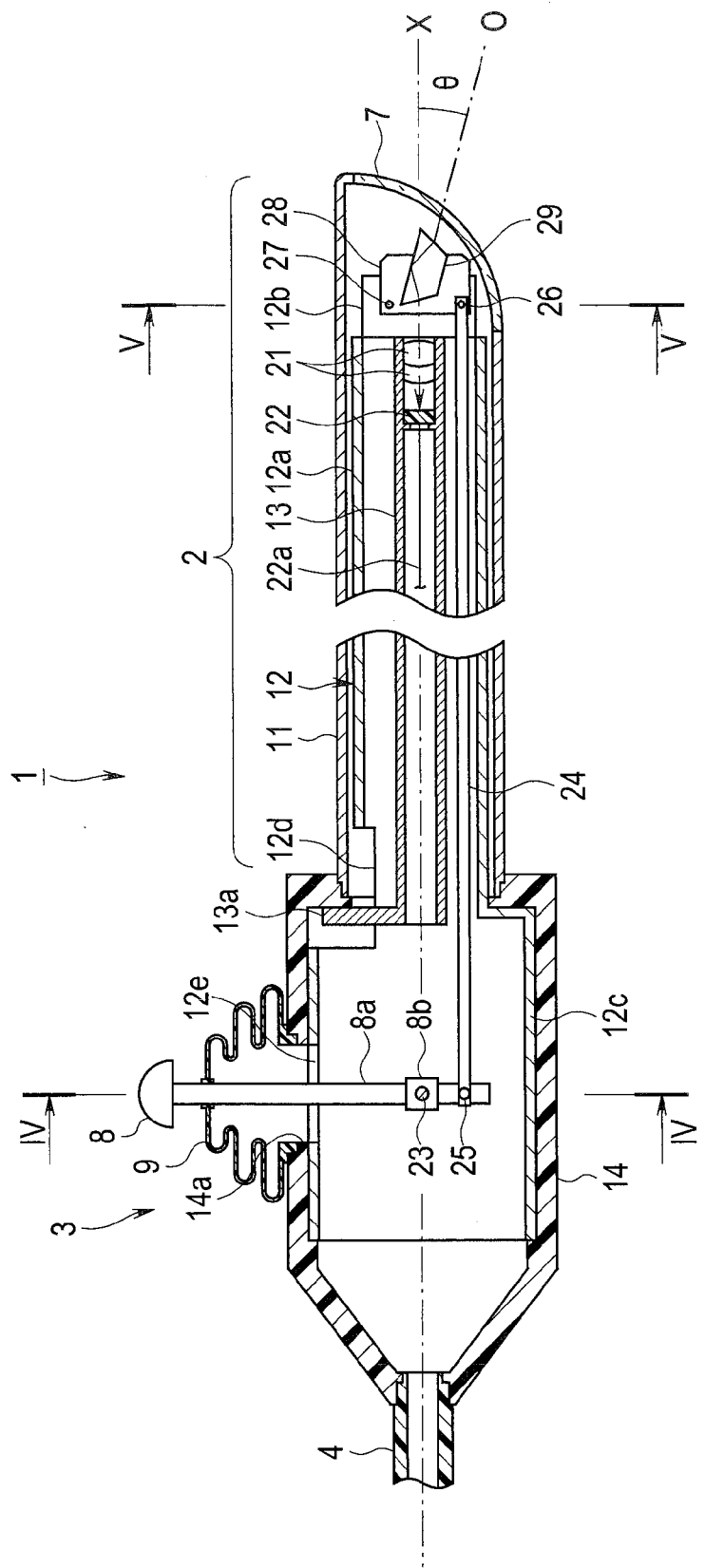
FIG. 2 is a cross-sectional view showing a configuration of the endoscope according to the first embodiment.
Figure 3:
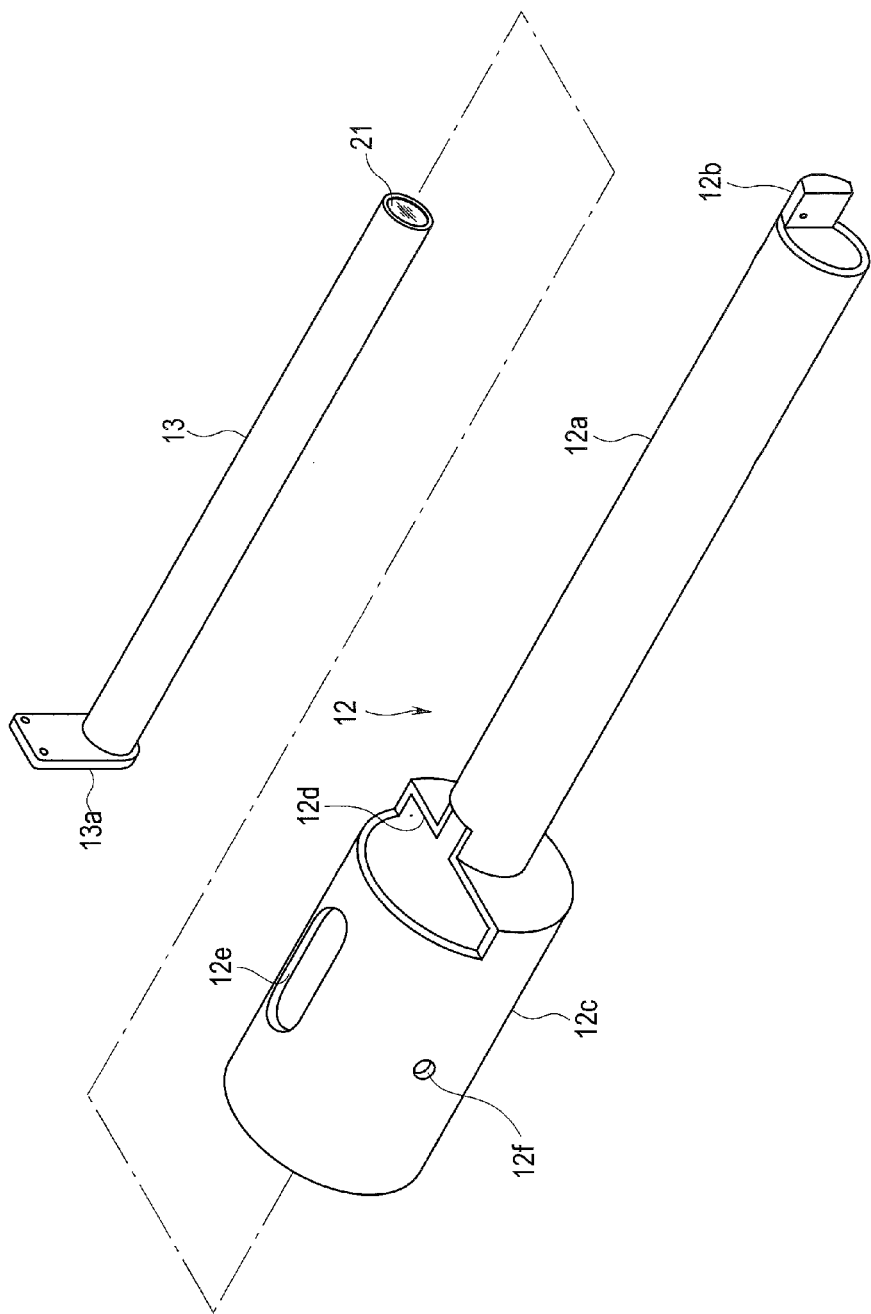
FIG. 3 is a perspective view showing configurations of a rotary cylinder and an image pickup system holding barrel according to the first embodiment.
Figure 4:
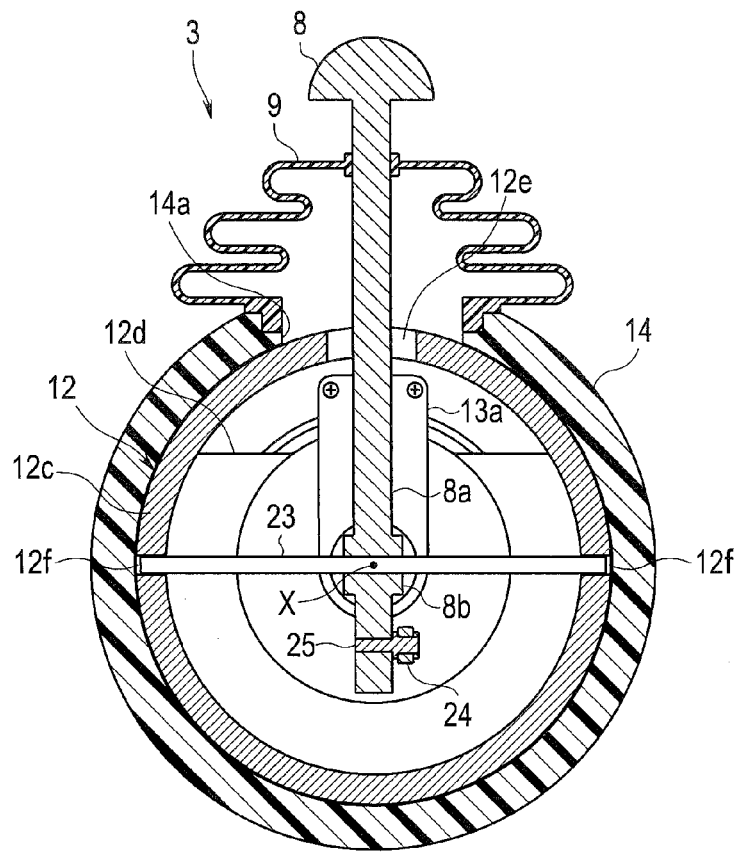
FIG. 4 is a cross-sectional view taken along IV-IV line in FIG. 2 according to the first embodiment.
Figure 5:
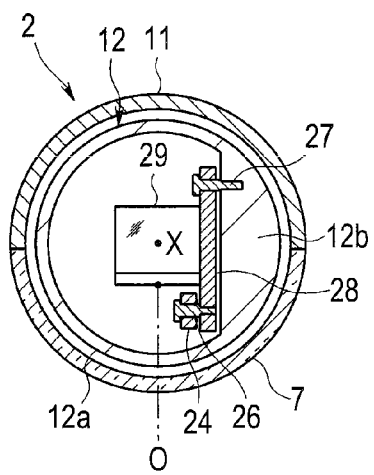
FIG. 5 is a cross-sectional view taken along V-V line in FIG. 2 according to the first embodiment.
Figure 6:
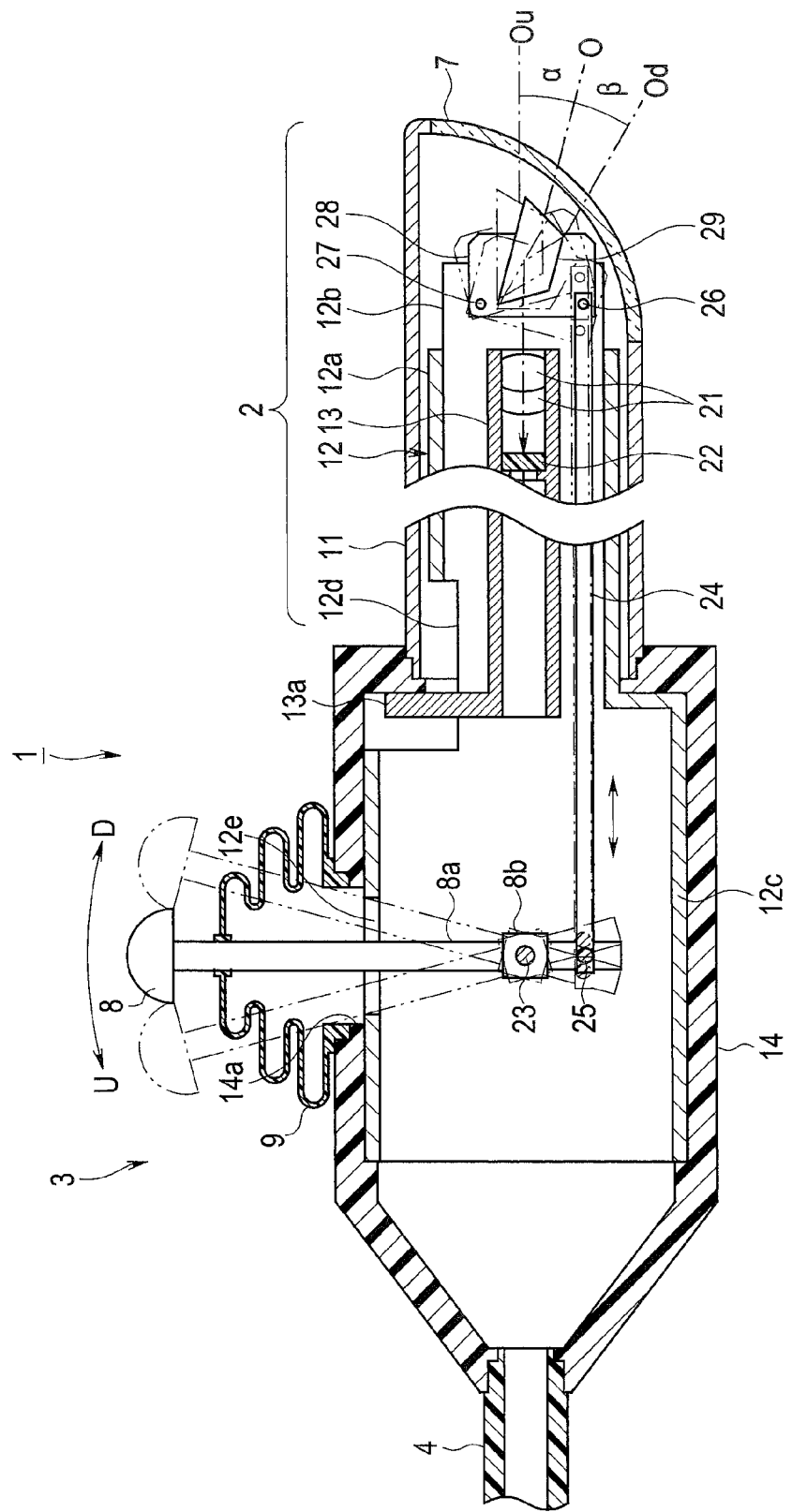
FIG. 6 is a cross-sectional view for illustrating a movement of the endoscope according to the first embodiment.
Figure 7:
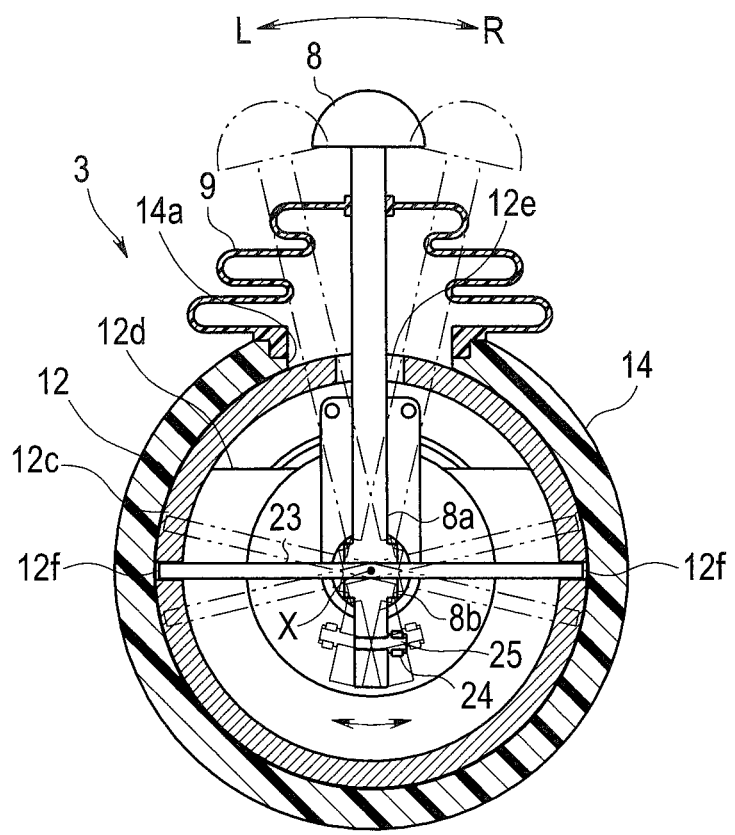
FIG. 7 is a cross-sectional view of an operation portion for illustrating a working of the endoscope according to the first embodiment.
Figure 8:
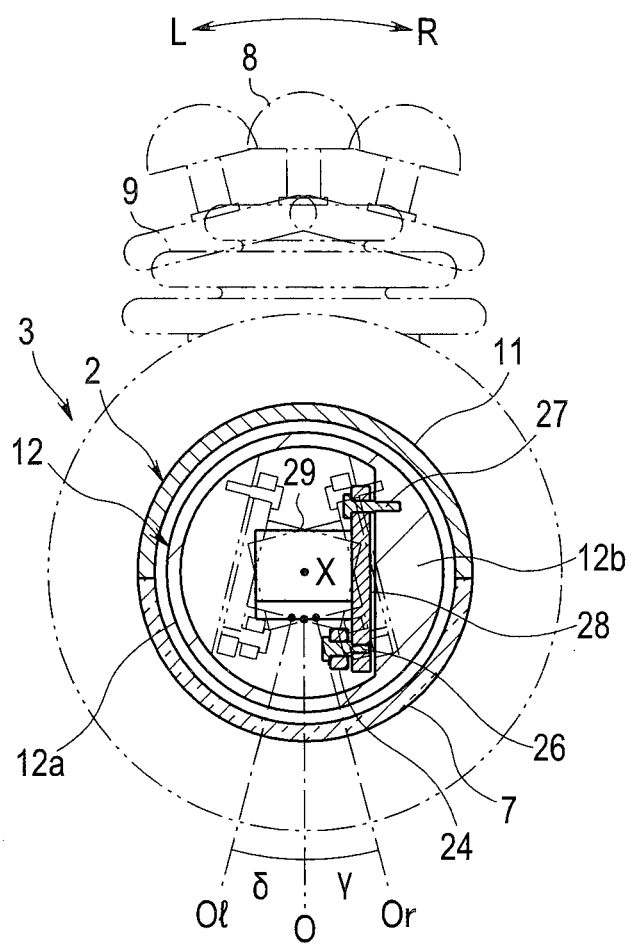
FIG. 8 is a cross-sectional view of a distal end part of an insertion portion for illustrating the working of the endoscope according to the first embodiment.

FIG. 1 is a perspective view showing an overall configuration of the endoscope; FIG. 2 is a cross-sectional view showing the configuration of the endoscope; FIG. 3 is a perspective view showing configurations of a rotary cylinder and an image pickup system holding barrel; FIG. 4 is a cross-sectional view taken along IV-IV line in FIG. 2; FIG. 5 is a cross-sectional view taken along V-V line in FIG. 2; FIG. 6 is a cross-sectional view for illustrating movement of the endoscope; FIG. 7 is a cross-sectional view of an operation portion for illustrating a working of the endoscope; and FIG. 8 is a cross-sectional view of a distal end part of an insertion portion for illustrating the working of the endoscope.

With reference to FIG. 1, description will be made on one example of a configuration of an endoscope 1 according to the present invention.

As shown in FIG. 1, the endoscope 1 according to the present embodiment is a medical device configured to be able to be introduced into a subject such as human body, and used, in particular, for surgical purpose, or for examination of urinary organs, and has a configuration for optically picking up an image of a predetermined site to be observed in the subject.

Note that the subject into which the endoscope 1 is introduced is not limited to a human body, and may be another living body, or artificial materials such as a machine, structure, or the like.

The endoscope 1 is configured mainly by a rigid insertion portion 2 configured to be introduced into a subject, an operation portion 3 located at the proximal end of the insertion portion 2, and a universal cord 4 extended from the proximal end portion of the operation portion 3. Note that the endoscope 1 in the present embodiment is a type in which the insertion portion 2 does not include a flexible portion, what is called a rigid endoscope, a laparoscope, a pyeloureteroscope, or the like.

The universal cord 4 includes, at the proximal end portion thereof, an endoscope connector 4a to be connected with an external apparatus 5 such as a video processor.

The external apparatus 5 is provided with an image processing section. The image processing section generates a video signal based on an image pickup device output signal outputted from the image pickup device to be described later, and outputs the generated video signal to an image display section 6 as a monitor. That is, in the present embodiment, an optical image (endoscopic image) picked up by the image pickup device is displayed on the image display section 6 as video.

The insertion portion 2 of the endoscope 1 includes, on the lower portion side of the distal end thereof, a dome-shaped cover glass 7 as an observation window.

The operation portion 3 of the endoscope 1 includes, at the center of top portion thereof, an operation lever 8 which is an operation member of what is called a joystick type, and a rubber boot 9 which is a cover body that covers the base part from which the operation lever 8 is protruded.

Next, detailed description will be made on the inner configuration of the endoscope 1 with reference to FIGS. 2 to 5.

As shown in FIG. 2, the insertion portion 2 of the endoscope 1 includes an exterior tube 11 which is an insertion pipe whose distal end lower portion side is sealed with the cover glass 7. Inside the exterior tube 11, a rotary cylinder 12 as a transmission member (second transmission member) is disposed. An image pickup system holding cylinder 13 is disposed in the rotary cylinder 12.

The proximal end of the exterior tube 11 is connected with the distal end of an operation portion casing 14 which is an exterior member of the operation portion 3. Note that the operation portion casing 14 has substantially a cylindrical shape, and includes, at the center of the upper portion thereof, an opening portion 14a to which the rubber boot 9 is fixed, and the proximal end side of the operation portion casing is formed in a tapered shape. The proximal end portion of the operation portion casing 14 is connected with the universal cord 4.

The rotary cylinder 12 includes: a small-diameter cylinder portion 12a, which is a third shaft, configured to be housed in the exterior tube 11; a protrusion portion 12b that protrudes from the distal end opening of the small-diameter cylinder portion 12a so as to have a plane portion; and a large-diameter cylinder portion 12c, which is a fourth shaft, provided continuously with the proximal end of the small-diameter cylinder portion 12a and held so as to be rotationally movable in the operation portion casing 14.

In addition, the rotary cylinder 12 includes a cutout portion 12d formed at the upper portion side of the boundary part between the small-diameter cylinder portion 12*a* and the large-diameter cylinder portion 12*c*, and a long hole 12*e* formed on the upper portion of the large-diameter portion 12*c* so as to be along the longitudinal axis direction, and shaft holding holes 12*f* (see FIG. 3) formed respectively on both sides of the large-diameter cylinder portion 12*c*.

The rotary cylinder 12 is held such that the outer circumferential surface of the large-diameter cylinder portion 12*c* contacts the inner circumferential surface of the operation portion casing 14, and disposed so as to be rotationally movable around the longitudinal axis (central axis X) in the exterior tube 11 and the operation portion casing 14.

Note that the rotary cylinder 12 may be configured such that the small-diameter cylinder portion 12*a* or (and) the large-diameter cylinder portion 12*c* is joined with the exterior tube 11 or (and) the operation portion casing 14 through a bearing for facilitating the rotational movement around the longitudinal axis.

The image pickup system holding cylinder 13 holds, inside the distal end thereof, a plurality of, i.e., two image formation lenses 21 constituting the image pickup optical system in the present embodiment, and includes an image pickup device 22 disposed at a position where the subject image is formed by two image formation lenses 21.

Note that the image pickup device 22 is a very small electronic part. The image pickup device 22 includes a plurality of elements, which output an electric signal corresponding to the incident light shown by the photographing optical axis O at a predetermined timing, are aligned on a planar light-receiving portion, and for example, the type called CCD (charge coupled device) or CMOS (complementary metal oxide semiconductor) sensor, or another kind of type is generally applied. The image pickup device 22 is connected to a circuit substrate and the like, not shown.

The image pickup device 22 is connected with an image pickup cable 22*a*. The image pickup cable 22*a* is inserted into the image pickup system holding cylinder 13, and disposed in the universal cord 4 through the inside of the operation portion casing 14 of the operation portion 3, to be connected to the endoscope connector 4*a* shown in FIG. 1.

In addition, the image pickup system holding cylinder 13 includes at the proximal end thereof a fixing plate portion 13*a* formed so as to be extended upward, and the fixing plate portion 13*a* is protruded through the cutout portion 12*d* of the rotary cylinder 12 and fixed to the inner surface of the distal end side upper portion of the operation portion casing 14 with a screw.

The insertion portion 2 is disposed such that the respective centers of the exterior tube 11, rotary cylinder 12, and image pickup system holding cylinder 13 coincide with one another. That is, the insertion portion 2 is disposed such that the central axis X along the longitudinal direction coincides with the respective central axes of the exterior tube 11, the rotary cylinder 12, and the image pickup system holding cylinder 13.

Furthermore, the operation portion casing 14 of the operation portion 3 is disposed such that the center thereof coincides with the central axis X. That is, the endoscope 1 according to the present embodiment includes the insertion portion 2 and the operation portion 3 which have the central axis X.

The operation lever 8 is provided with a block-shaped shaft receiving portion 8*b* which serves as a bearing disposed at the halfway portion of the operation rod 8*a*. A shaft 23 which serves as a rotary shaft, which is a second shaft, is inserted and fixed in the shaft receiving portion 8*b* by press fitting or the like.

As shown in FIGS. 2 and 4, both end portions of the shaft 23 are engageably inserted in shaft holding holes 12*f* formed respectively on the both side portions of the large-diameter cylinder portion 12*c* of the rotary cylinder 12 and held so as to be rotationally movable.

In addition, the shaft 23 is disposed such that the center thereof coincides with the respective centers of the rotary cylinder 12 and image pickup system holding cylinder 13. That is, the shaft 23 is disposed such that the center thereof is located on the central axis X of the insertion portion 2 and the operation portion 3.

Note that the operation rod 8*a* of the operation lever 8 includes a rotary shaft member 25 for holding the one end of the transmission rod 24 which is a rigid first transmission member so as to be rotationally movable, and the rotary shaft member 25 is screwed at the end part of the operation rod 8*a* located in the large-diameter cylinder portion 12*c* in the rotary cylinder 12.

The rotary shaft member 25 includes a shaft portion screwed to the operation rod 8*a* and a nut screwed to the end portion of the shaft portion, and holds the transmission rod 24 in which the shaft portion is inserted, so as to be rotationally movable but so as not to be fallen off by fastening of the nut.

The transmission rod 24 is extended from inside the large-diameter cylinder portion 12*c* of the rotary cylinder 12 as the second transmission member, which located in the operation portion 3, to the inside the small-diameter cylinder portion 12*a*, and the other end of the transmission rod 24 which is located in the insertion portion 2 is connected, so as to be rotationally movable, to a lower corner portion on the proximal end side of the plate-like optical element holding member 28, through a rotary shaft member 26 similar to the one as described above.

As shown in FIGS. 2 and 5, the optical element holding member 28 is provided with a trapezoidal prism 29 which is an optical element. The other corner portion on the proximal end side of the optical element holding member 28 is connected so as to be rotationally movable to the protrusion portion 12*b* disposed at the distal end of the small-diameter cylinder portion 12*a* of the rotary cylinder 12, through a rotary shaft 27 which is a first shaft. Note that the shaft direction of the rotary shaft member 26 and the rotary shaft 27 provided at the distal end part of the insertion portion 2 is parallel to the shaft direction of the shaft 23 provided in the operation portion 3.

That is, the operation lever 8 and the optical element holding member 28 are connected with each other by what is called a parallel link through the transmission rod 24.

In addition, the optical element holding member 28 includes one surface on which the trapezoidal prism 29 is provided and the other surface opposite to the one surface, and the other surface is disposed so as to face the plane of the protrusion portion 12*b*.

The trapezoidal prism 29 is configured to cause the light along the photographing optical axis O inclined downward by a predetermined angle θ with respect to the central axis X of the insertion portion 2 to enter the image pickup device 22 held by the image pickup system holding cylinder 13 through the image formation lenses 21 when the operation lever 8 of the operation portion 3 is in the initial neutral position at which the operation lever 8 is not tilted.

That is, the trapezoidal prism 29 is bonded to the optical element holding member 28 by adhesive or the like so as to be tilted by the predetermined angle θ, with the short base side of the prism positioned on the lower side.

The endoscope 1 according to the present embodiment that is configured as described above enables the direction of view to be changed upward, downward, leftward and rightward by the tilting operations of the operation lever 8 provided at the operation portion 3.

Specifically, as shown in FIG. 6, in the endoscope 1, when the operation lever 8 provided at the operation portion 3 is tilted forward or backward (in the direction of the arrow U/D in the drawing) from the initial position, the operation lever 8 swings around the shaft 23.

At this time, in conjunction with the movement of the operation rod 8*a* of the operation lever 8, the transmission rod 24 connected to the operation rod 8*a* moves forward or backward along the longitudinal direction of the insertion portion 2.

In accordance with the forward or backward movement of the transmission rod 24, the optical element holding member 28 connected to the distal end of the transmission rod 24 through the rotary shaft member 26 moves rotationally around the rotary shaft 27. This causes the angle of the trapezoidal prism 29 with respect to the central axis X of the insertion portion 2 to be changed, the trapezoidal prism 29 being an optical element provided at the optical element holding member 28.

Note that, according to the endoscope 1 of the present embodiment, when the operation lever 8 provided at the operation portion 3 is tilted forward (the direction of arrow D in the drawing) from the initial position, the transmission rod 24 moves backward to pull the optical element holding member 28 backward.

As a result, the optical element holding member 28 is rotationally moved downward, to cause the trapezoidal prism 29 provided at the optical element holding member 28 to be tilted downward.

This causes the light along the photographing optical axis Od, which is inclined downward by a predetermined angle β with respect to the light along the photographing optical axis O, to be incident on the trapezoidal prism 29, and the incident light is image-formed by the image pickup device 22 through the image formation lenses 21 held by the image pickup system holding cylinder 13, in the endoscope 1.

That is, when the operation lever 8 provided at the operation portion 3 is tilted forward (in the direction of the arrow D in the drawing) from the initial position, the direction of view of the endoscope 1 is changed downward (DOWN).

On the other hand, in the endoscope 1, when the operation lever 8 provided at the operation portion 3 is tilted backward (in the direction of the arrow U in the drawing) from the initial position, the transmission rod 24 moves forward, to push the optical element holding member 28 forward.

Therefore, the optical element holding member 28 is rotationally moved upward, to cause the trapezoidal prism 29 provided at the optical element holding member 28 to be tilted upward.

As a result, in the endoscope 1, the light along the photographing optical axis Ou, which is inclined upward by the predetermined angle α with respect to the light along the photographing optical axis O, is incident on the trapezoidal prism 29, and the incident light is image-foliated by the image pickup device 22 through the image formation lenses 21.

That is, when the operation lever 8 provided at the operation portion 3 is tilted backward (in the direction of the arrow U in the drawing) from the initial position, the direction of view of the endoscope 1 is changed upward (UP).

Thus, the direction of view of the endoscope 1 can be changed upward and downward by the forward and backward tilting operations of the operation lever 8 provided at the operation portion 3.

In addition, as shown in FIG. 7, in the endoscope 1, when the operation lever 8 provided at the operation portion 3 is tilted leftward or rightward (the direction of L/R in the drawing) from the initial position, the rotary cylinder 12 disposed in the operation portion 3 and the insertion portion 2 moves rotationally around the center (central axis X).

That is, in the endoscope 1, in accordance with the tilting operation of the operation lever 8, a rotational force is applied to the large-diameter cylinder portion 12*c* through the shaft 23 fixed to the operation rod 8*a* of the operation lever 8, to cause the rotary cylinder 12, together with the small-diameter cylinder portion 12*a*, to move rotationally around the central axis X in the operation portion casing 14 of the operation portion 3 and the exterior tube 11.

Therefore, as shown in FIG. 8, also the optical element holding member 28 disposed at the protrusion portion 12*b* located at the distal end of the small-diameter cylinder portion 12*a* moves rotationally around the central axis X. This causes the trapezoidal prism 29 fixed to the optical element holding member 28 to move rotationally around the central axis X, and the angle of the trapezoidal prism 29 around the central axis X is changed.

Note that, in the endoscope 1 according to the present embodiment, when the operation lever 8 provided at the operation portion 3 is tilted leftward (in the direction of the arrow L in the drawing) from the initial position, also the rotary cylinder 12 moves rotationally in the counterclockwise direction.

This causes the optical element holding member 28 to be moved rotationally in the counterclockwise direction, to thereby cause the trapezoidal prism 29 provided at the optical element holding member 28 to be tilted rightward.

Then, in the endoscope 1, the light along the photographing optical axis Or, which is inclined rightward by the predetermined angler with respect to the light along the photographing optical axis O, is incident on the trapezoidal prism 29, and the incident light is image-formed by the image pickup device 22 through the image formation lenses 21 held by the image pickup system holding cylinder 13.

That is, in the endoscope 1, when the operation lever 8 provided at the operation portion 3 is tilted leftward (in the direction of the arrow L in the drawing) from the initial position, the direction of view with respect to the subject is changed rightward (Right) which is opposite to the operation direction of the operation lever.

On the other hand, in the endoscope 1, when the operation lever 8 provided at the operation portion 3 is tilted rightward (in the direction of the arrow R in the drawing) from the initial position, also the rotary cylinder 12 moves rotationally in the clockwise direction.

As a result, the optical element holding member 28 is moved rotationally in the clockwise direction, to cause the trapezoidal prism 29 provided at the optical element holding member 28 to be tilted leftward.

Then, in the endoscope 1, the light along the photographing optical axis Ol, which is inclined leftward by the predetermined angle δ with respect to the light along the photographing optical axis O, is incident on the trapezoidal prism 29, and the incident light is image-formed by the image pickup device 22 through the image formation lenses 21.

That is, in the endoscope 1, when the operation lever 8 provided at the operation portion 3 is tilted rightward (in the direction of the arrow R in the drawing) from the initial position, the direction of view with respect to the subject is changed leftward (Left) which is opposite to the operation direction of the operation lever.

Thus, the direction of view of the endoscope 1 can be changed leftward and rightward by the leftward and rightward tilting operations of the operation lever 8 provided at the operation portion 3.

Therefore, the direction of view of the endoscope 1 can be changed upward, downward, leftward and rightward by the forward, backward, leftward and rightward tilting operations of the operation lever 8 provided at the operation portion 3.

As described above, the endoscope 1 according to the present embodiment is capable of moving the direction of view upward, downward, leftward, and rightward with the operation lever 8 which is one of the operation members provided at the operation portion 3, at the time of deflecting the optical axis in upward, downward, leftward and rightward directions by tilting and rotationally moving the trapezoidal prism 29 provided at the distal end of the insertion portion 2.

Thus, with the endoscope 1, the user such as a doctor is capable of changing the view intuitively by a single action operation in an intended direction and to an intended site while viewing an image of an operated part on an image display section 6 which is a monitor, during the operation. That is, the operability in changing the view is improved.

First Modified Example

Figure 9:
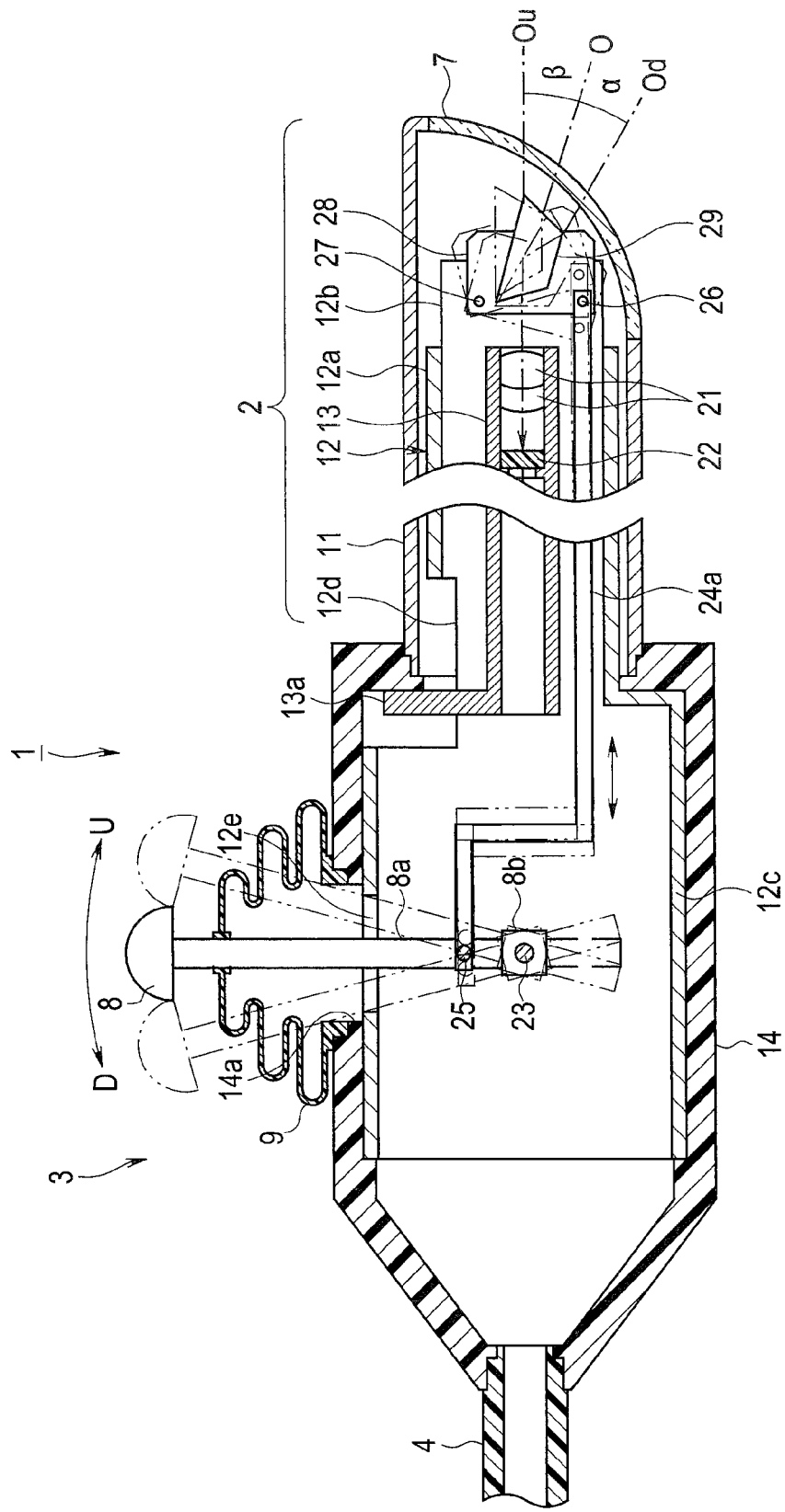
FIG. 9 is a cross-sectional view showing a configuration of an endoscope according to a first modified example of the first embodiment.

FIG. 9 is a cross-sectional view showing a configuration of an endoscope according to a first modified example.

As shown in FIG. 9, the endoscope 1 may be configured such that a crank-shaped transmission rod 24a, which serves as a first transmission member in this modified example, that moves forward or backward in accordance with the forward or backward tilting operation of the operation lever 8 provided at the operation portion 3 is provided, to change the angle of the trapezoidal prism 29 provided at the optical element holding member 28 with respect to the central axis X of the insertion portion 2.

Specifically, the transmission rod 24a has the crank shape flexed upward and backward in the operation portion 3, and the end portion on the proximal end side of the transmission rod is held so as to be rotationally movable by the rotary shaft member 25 at the halfway position of the operation rod 8a of the operation lever 8, the halfway position being located on the upper side with respect to the shaft receiving portion 8b on the operation rod 8a.

Also in the endoscope 1 thus configured, when the operation lever 8 provided at the operation portion 3 is tilted forward or backward (in the direction of the arrow U/D in the drawing) from the initial position, the transmission rod 24a connected to the operation rod 8a moves forward or backward along the longitudinal direction of the insertion portion 2.

However, the endoscope 1 according to the present modified example is different from the one in the embodiment as described above, and when the operation lever 8 provided at the operation portion 3 is tilted forward (in the direction of the arrow U in the drawing) from the initial position, the transmission rod 24a moves forward, to thereby push the optical element holding member 28 forward. As a result, the optical element holding member 28 is rotationally moved upward to cause the trapezoidal prism 29 provided at the optical element holding member 28 to be tilted upward.

That is, in the endoscope 1, when the operation lever 8 provided at the operation portion 3 is tilted forward (in the direction of the arrow U in the drawing) from the initial position, the direction of view with respect to the subject is changed upward (UP).

On the other hand, in the endoscope 1, when the operation lever 8 provided at the operation portion 3 is tilted backward (in the direction of the arrow D in the drawing) from the initial position, the transmission rod 24a moves backward to thereby pull the optical element holding member 28 backward. As a result, the optical element holding member 28 is rotationally moved downward to cause the trapezoidal prism 29 provided at the optical element holding member 28 to be tilted downward.

That is, in the endoscope 1, when the operation lever 8 provided at the operation portion 3 is tilted backward (in the direction of the arrow D in the drawing) from the initial position, the direction of view with respect to the subject is changed downward (DOWN).

Even if the endoscope 1 is thus configured, unlike the one as described above, it is possible to reverse the forward and backward tilting operation directions of the operation lever 8 at the time of changing the direction of view upward and downward.

Second Modified Example

Figure 10:
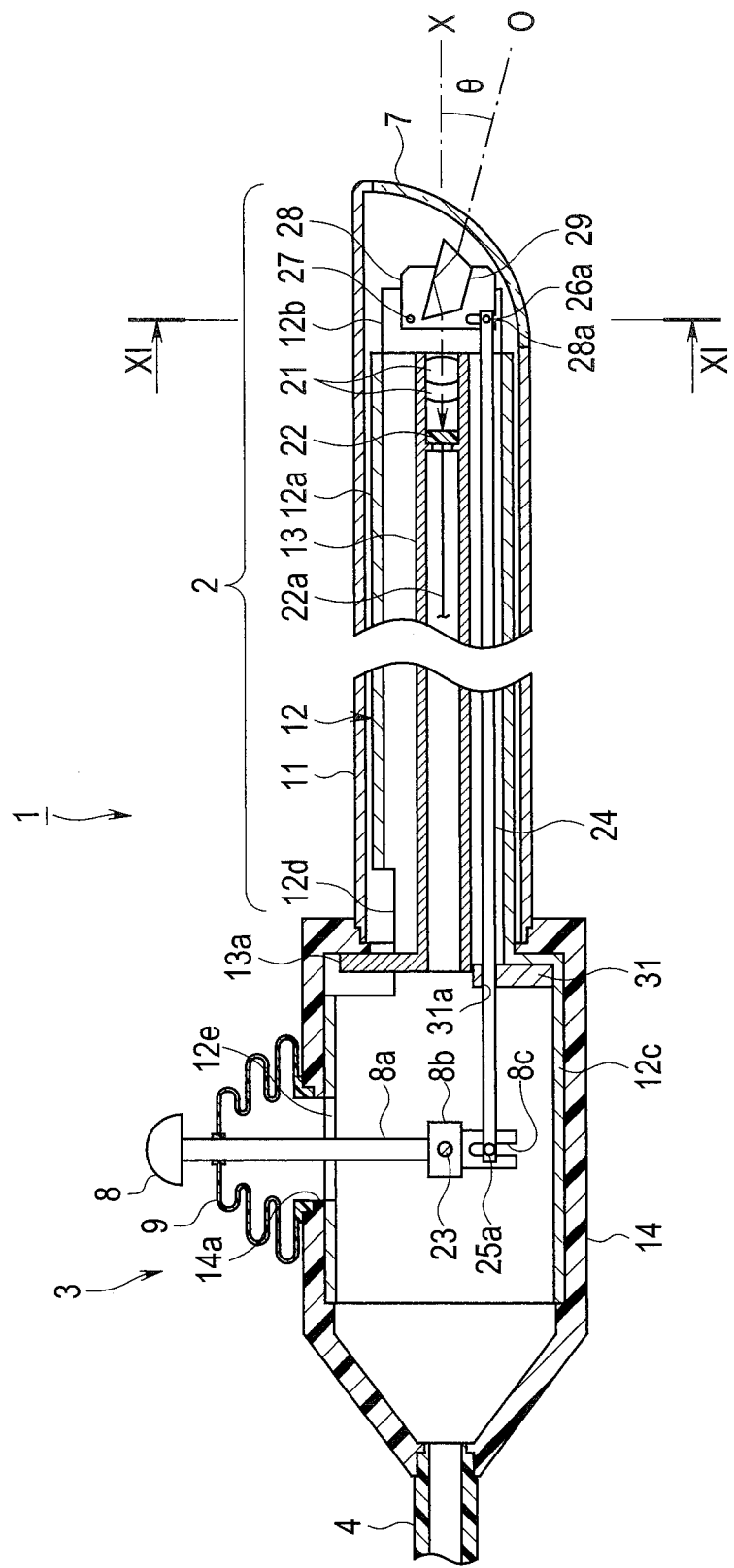
FIG. 10 is a cross sectional view for illustrating a configuration of an endoscope according to a second modified example of the first embodiment.
Figure 11:
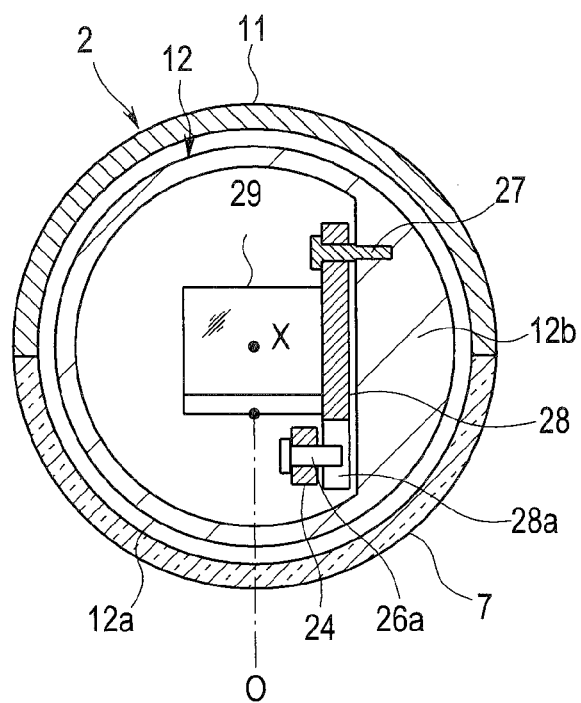
FIG. 11 is a cross-sectional view showing a configuration of a distal end part of the endoscope according to the second modified example of the first embodiment.

FIG. 10 is a cross sectional view for illustrating a configuration of an endoscope according to a second modified example; FIG. 11 is a cross-sectional view showing a configuration of a distal end part of the endoscope; and FIG. 12 is a perspective view showing a configuration of a guide that rectilinearly guides the transmission rod.

As shown in FIG. 10 and FIG. 11, the transmission rod 24 includes shaft pins 25a, 26a respectively on both end parts, and may be configured such that the shaft pin 25a and the shaft pin 26a are engageably inserted in an operation portion side slit 8c formed on the operation lever 8 and a holding member side slit 28a formed on the optical element holding member 28, respectively.

That is, the shaft pins 25a, 26a disposed respectively on the both ends of the transmission rod 24 are engageably inserted in the operation portion side slit 8c and the holding member side slit 28a, respectively, so as to be fit in the width dimensions of the slits.

Figure 12:
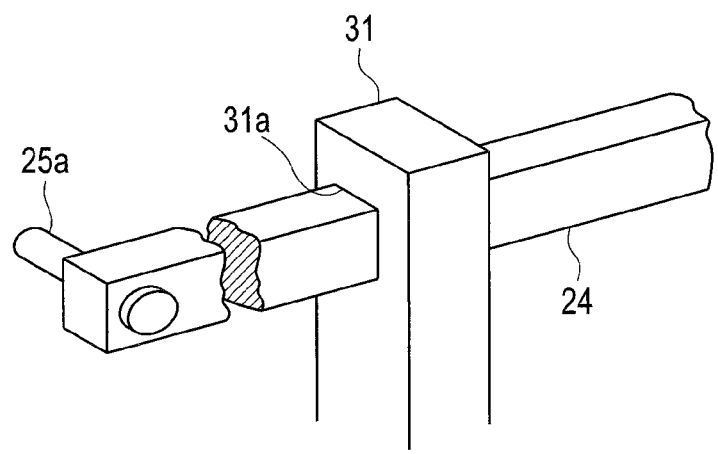
FIG. 12 is a perspective view showing a configuration of a guide that rectilinearly guides a transmission rod according to the second modified example of the first embodiment.

In addition, as shown in FIG. 12, the transmission rod 24 in the present modified example has a square pole shape, and is inserted through a hole portion 31a formed on a rectangular block-shaped guide 31 fixed to the large-diameter cylinder portion 12c of the rotary cylinder 12, to be guided rectilinearly.

With the endoscope 1 thus configured, the transmission rod 24 can be configured to move forward or backward along the longitudinal direction without being moved in the upward or downward direction in the state rectilinearly guided through the hole portion 31a of the guide 31 in accordance with the forward or backward tilting operation of the operation lever 8 provided at the operation portion 3.

Third Modified Example

Figure 13:
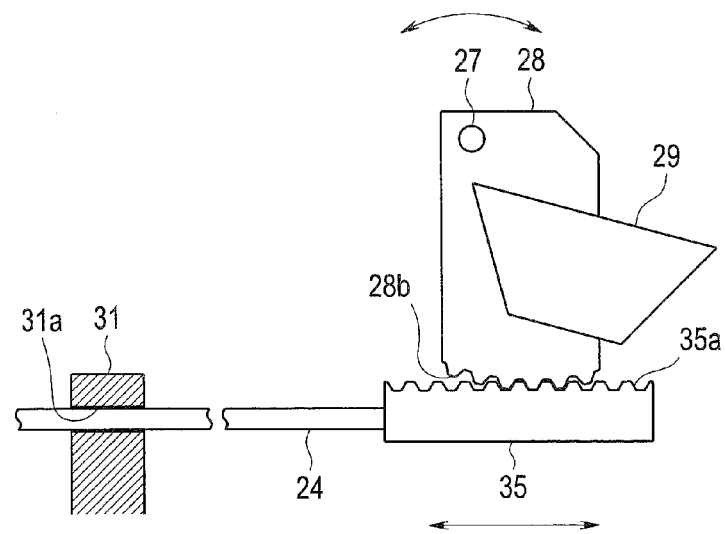
FIG. 13 shows a rack-and-pinion configuration for rotationally moving an optical element holding member provided with a trapezoidal prism by a transmission rod according to a third modified example of the first embodiment.
Figure 14:
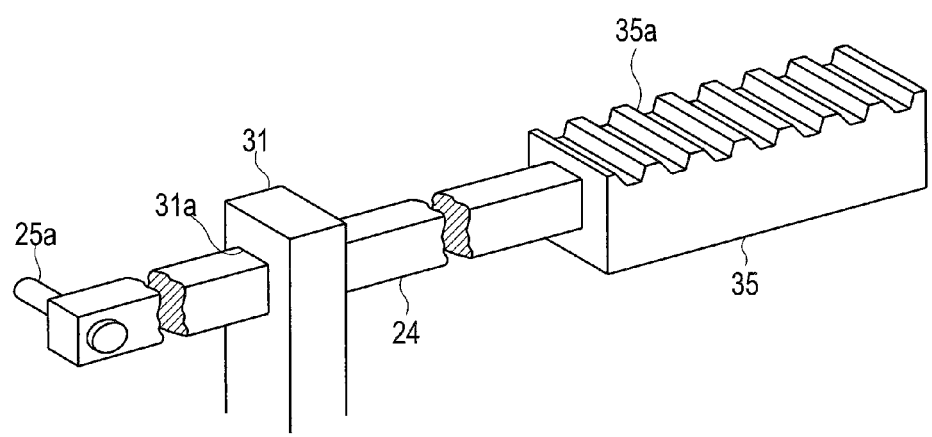
FIG. 14 is a perspective view showing a configuration of a transmission rod rectilinearly guided by a guide according to the third modified example of the first embodiment.

FIG. 13 shows a rack-and-pinion configuration for rotationally moving the optical element holding member provided with the trapezoidal prism by a transmission rod according to a third modified example; and FIG. 14 is a perspective view showing the configuration of the transmission rod rectilinearly guided by the guide.

As shown in FIG. 13 and FIG. 14, by further modifying the second modified example, the transmission rod 24, which serves a first transmission member in this modified example, that moves forward or backward by the tilting operation of the operation lever 8 provided at the operation portion 3 may include at the distal end part thereof a block-shaped rack gear portion 35 having a rack gear 35a formed on the top surface, and may be configured such that the rack gear portion 35 meshes with a pinion gear 28b formed along an arc shape at the lower portion of the optical element holding member 28 and moves forward or backward, to cause the optical element holding member 28 to which the trapezoidal prism 29 is provided to move rotationally around the rotary shaft 27.

That is, the optical element holding member 28 to which the trapezoidal prism 29 is provided is moved rotationally around the rotary shaft 27 with the rack and pinion configuration by the transmission rod 24.

Also the endoscope 1 thus configured is capable of changing the direction of view upward and downward by the forward and backward tilting operations of the operation lever 8.

Fourth Modified Example

Figure 15:
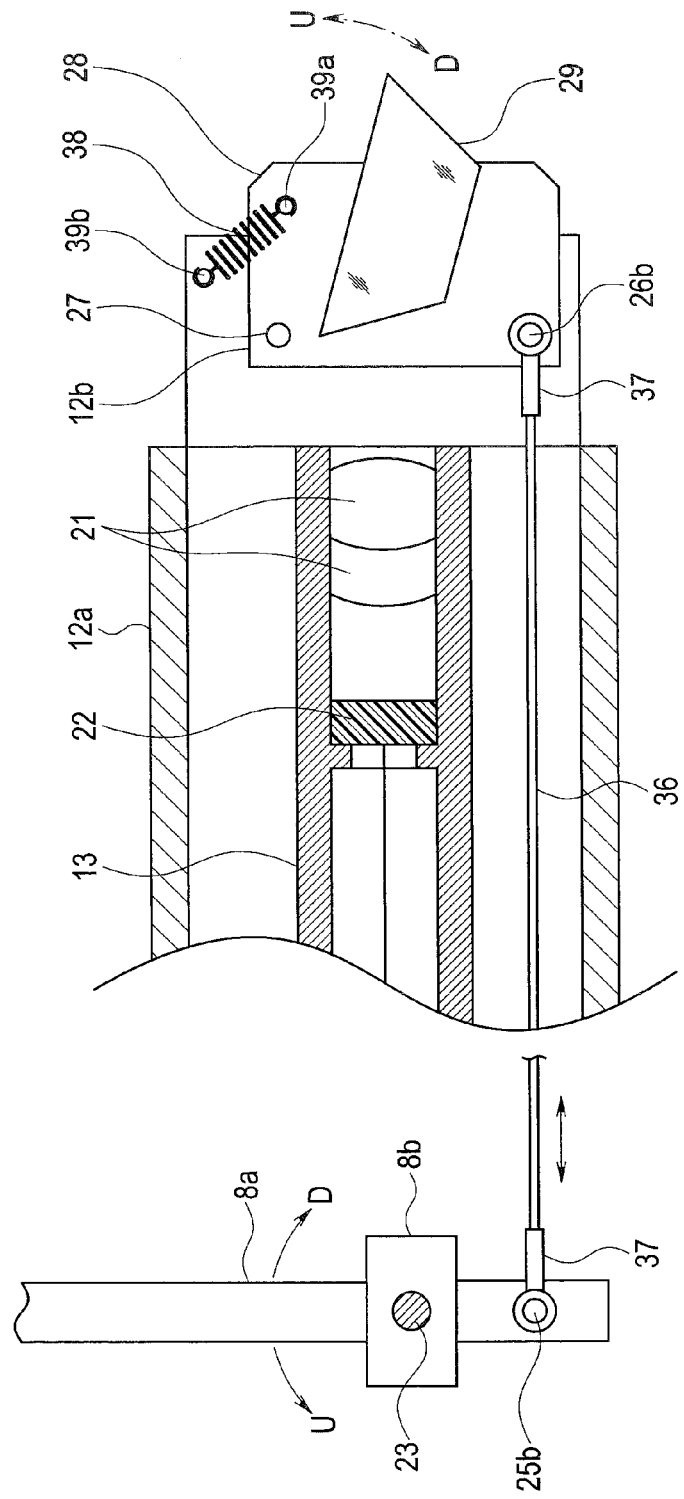
FIG. 15 schematically shows a configuration for rotationally moving an optical element holding member provided with a trapezoidal prism by a wire according to a fourth modified example of the first embodiment.
Figure 16:
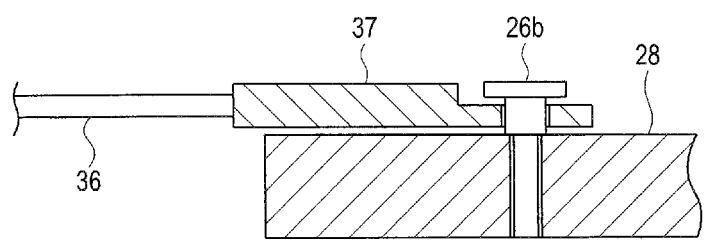
FIG. 16 is a cross-sectional view showing a configuration of a wire clamp which is inserted into a pin and connected thereto so as to be rotationally movable, according to the fourth modified example of the first embodiment.

FIG. 15 schematically shows the configuration for rotationally moving the optical element holding member provided with the trapezoidal prism by the wire according to the fourth modified example, and FIG. 16 is a cross-sectional view showing a configuration of a wire clamp which is inserted into a pin and connected thereto so as to be rotationally movable.

As shown in FIG. 15, a wire 36, which serves as a first transmission member in this modified example, may be used as the transmission member for rotationally moving the optical element holding member 28 to which the trapezoidal prism is provided by the tilting operation of the operation lever 8 provided at the operation portion 3.

Specifically, the wire 36 is connected, so as to be rotationally movable, to the lower end portion of the operation rod 8a of the operation lever 8 and to the lower corner portion on the proximal end side of the optical element holding member 28.

In addition, a tension spring 38, which contracts upward to pull the optical element holding member 28, is provided between the optical element holding member 28 and the protrusion portion 12b protruded from the small-diameter cylinder portion 12a of the rotary cylinder 12.

The tension spring 38 has one end latched on a spring locking pin 39a provided at the upper corner portion of the front side of the optical element holding member 28 and another end latched on a spring locking pin 39b provided at the upper corner portion of the front side of the protrusion portion 12b.

The wire 36 includes wire clamps 37 disposed respectively on both ends of the wire. One of the wire clamps 37 is, as shown in FIG. 16, for example, inserted in a pin 26b which is pivoted to the lower corner portion on the proximal end side of the optical element holding member 28 and has an outward flange, and the one of the wire clamps 37 is connected at the pin 26b so as be rotationally movable.

Note that the other of the wire clamps 37 is, similarly as the one of the wire clamps 37 shown in FIG. 16, inserted in a pin 25b which is pivoted to the lower end portion of the operation rod 8a and has an outward flange, and the other of the wire clamps 37 is connected at the pin 25b so as to be rotationally movable, though not shown.

In the endoscope 1 thus configured, when the operation lever 8 provided at the operation portion 3 is tilted forward (in the direction of the arrow D in FIG. 15) from the initial position, the wire 36 is pulled to cause the optical element holding member 28 to rotationally move downward around the rotary shaft 27 against the tensile force of the tension spring 38.

Further, in the endoscope 1, when the operation lever 8 provided at the operation portion 3 is tilted backward (in the direction of the arrow U in FIG. 15) from the initial position, the wire 36 is relaxed to cause the optical element holding member 28 to rotationally move upward around the rotary shaft 27 by the tensile force of the tension spring 38.

That is, in the endoscope 1, the optical element holding member 28 to which the trapezoidal prism 29 is provided is moved rotationally around the rotary shaft 27 by the forward or backward movement of the wire 36 which is pulled or relaxed by the tilting operation of the operation lever 8 provided at the operation portion 3.

Even if the endoscope 1 is thus configured, the direction of view can be changed upward and downward by the forward and backward tilting operations of the operation lever 8.

Second Embodiment

Next, an endoscope according to the second embodiment of the present invention will be described with reference to drawings.

Note that the constituent elements same as those in the first embodiment are attached with the same reference numerals, and detailed descriptions thereof will be omitted in the description below.

Figure 17:
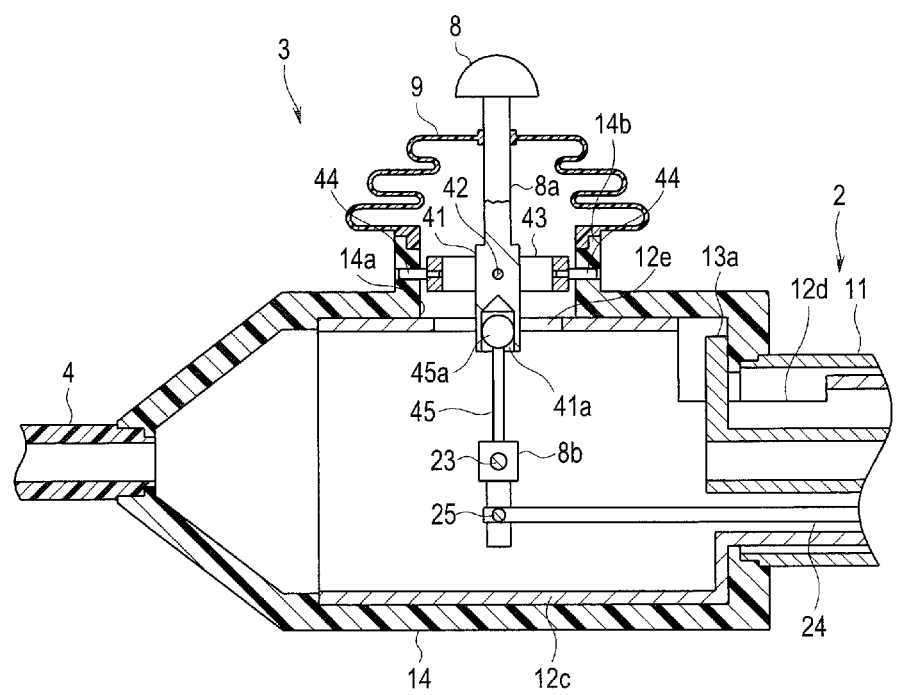
FIG. 17 is a cross-sectional view showing a configuration of an operation portion of an endoscope according to a second embodiment.
Figure 18:
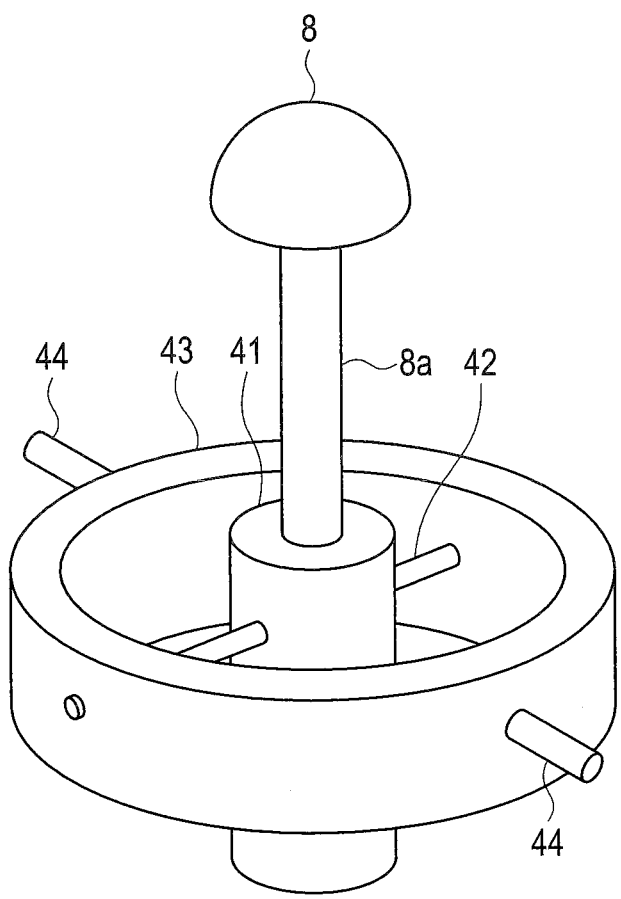
FIG. 18 is a perspective view showing a configuration of the operation lever according to the second embodiment.
Figure 19:
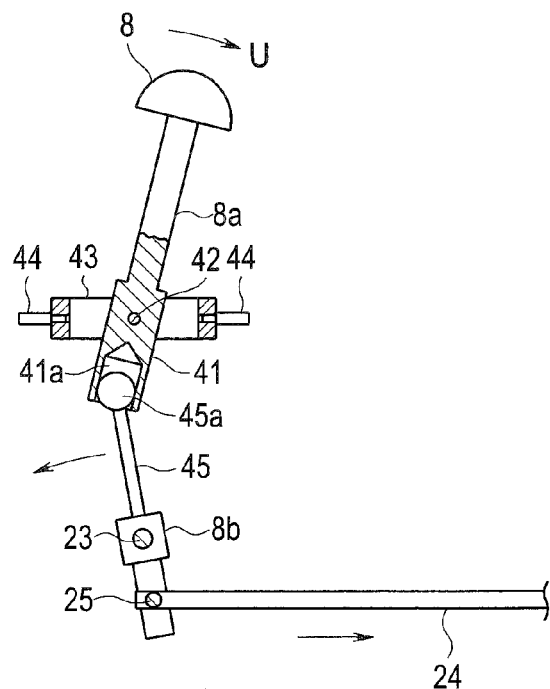
FIG. 19 illustrates a movement in a state where the operation lever is tilted forward, according to the second embodiment.
Figure 20:
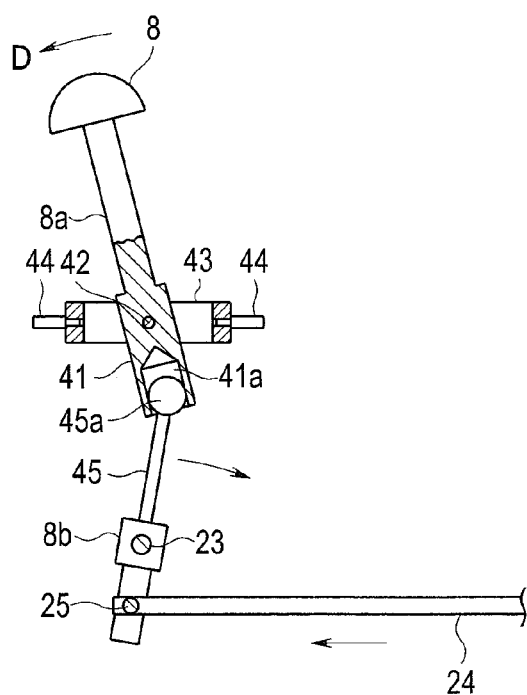
FIG. 20 illustrates a movement in a state where the operation lever is tilted backward, according to the second embodiment.
Figure 21:
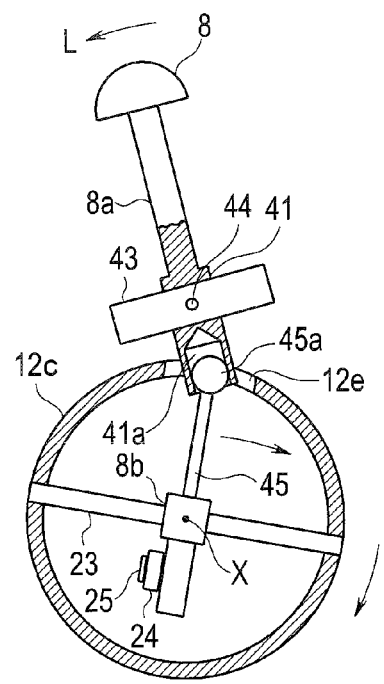
FIG. 21 illustrates a movement in a state where the operation lever is tilted leftward, according to the second embodiment.
Figure 22:
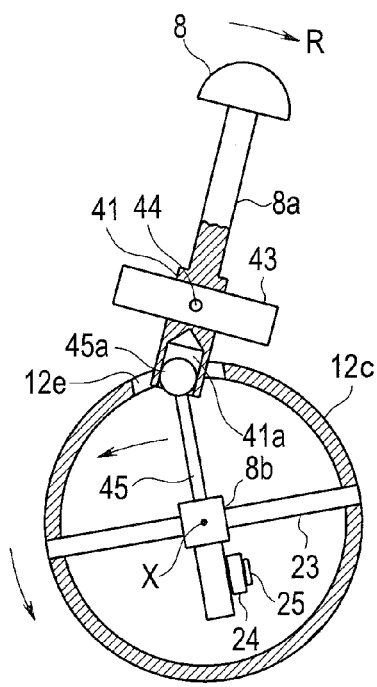
FIG. 22 illustrates a movement in a state where the operation lever is tilted rightward, according to the second embodiment.

FIG. 17 is a cross-sectional view showing the configuration of the operation portion of the endoscope, FIG. 18 is a perspective view showing the configuration of the operation lever, FIG. 19 illustrates the movement in the state where the operation lever is tilted forward, FIG. 20 illustrates the movement in the state where the operation lever is tilted backward, FIG. 21 illustrates the movement in the state where the operation lever is tilted leftward, and FIG. 22 illustrates the movement in the state where the operation lever is tilted rightward.

As shown in FIGS. 17 and 18, the endoscope 1 according to the present embodiment is different from the one in the first embodiment in the configuration of the operation lever 8 for changing the direction of view, which is provided at the operation portion 3.

In detail, the operation lever 8 includes a columnar portion 41 at the lower end of the operation rod 8a. The columnar portion 41 includes a cylindrical hole 41a formed from the lower end surface toward the inner portion of the columnar portion. In addition, the columnar portion 41 includes a rotary shaft 42, as a second shaft in the present embodiment penetrated and fixed at the upper portion of the cylindrical hole 41a.

The rotary shaft 42 has both ends held so as to be rotationally movable by a ring member 43 provided in the circumferential direction of the columnar portion 41, and the operation rod 8a is disposed so as to be rotationally movable around the rotary shaft 42 with respect to the ring member 43.

Note that the rotary shaft 42 has the longitudinal axis in the left/right direction of the operation portion 3, and the operation rod 8a swings around the longitudinal axis, to cause the operation lever 8 to tilt forward and backward direction.

The ring member 43 has rotary shaft pins 44, which serve as fourth shafts in the present embodiment, pivoted respectively to two portions on the outer circumferential portion, in the direction perpendicular to the rotary shaft 42. The two rotary shaft pins 44 are held so as to be rotationally movable by a cylindrical portion 14b that protrudes upward in a cylindrical shape from the opening portion 14a of the operation portion casing 14.

That is, the ring member 43 disposed so as to be housed in the cylindrical portion 14b and so as to be rotationally movable around the two rotary shaft pins 44.

Note that the two rotary shaft pins 44 include a longitudinal axis in the forward/backward direction of the operation portion, and the ring member 43 moves rotationally around the longitudinal axis, to cause the operation lever 8 to tilt in the leftward and rightward directions.

In addition, in the cylindrical hole 41a of the columnar portion 41, a spherical portion 45a provided at the upper end portion of a tilt rod 45 is engageably inserted. At the lower end portion of the tilt rod 45, the shaft receiving portion 8b into which the shaft 23 serving as a rotary shaft is inserted and fixed is provided similarly as in the first embodiment, and the rotary shaft member 25 that holds the one end of the transmission rod 24 so as to be rotationally movable is provided below the shaft receiving portion 8b.

When the operation lever 8 is tilted, the spherical portion 45a moves rotationally and moves upward or downward in the cylindrical hole 41a of the columnar portion 41 and the tilt rod 45, which, together with the transmission rod 24, configures a first transmission member in the present embodiment, swings around the shaft 23. At this time, the tilt rod 45 tilts in the direction opposite to the tilting direction of the operation lever 8.

In conjunction with the movement of the operation rod 8a of the operation lever 8, the transmission rod 24 connected to the operation rod 8a moves forward or backward along the longitudinal direction of the insertion portion 2.

In the endoscope 1 configured as described above, as shown in FIG. 19, when the operation lever 8 is tilted forward (the direction of the arrow U in the drawing) from the initial position, the operation rod 8a is tilted forward around the rotary shaft 42, and the tilt rod 45, which has the spherical portion 45a engageably inserted into the cylindrical hole 41a of the columnar portion 41 provided at the operation rod 8a, is tilted backward around the shaft 23, to thereby cause the transmission rod 24 to move forward.

Then, the forward movement of the transmission rod 24 causes the optical element holding member 28, not shown here, to be pushed forward, and thereby the optical element holding member 28 is rotationally moved upward. As a result, the trapezoidal prism 29 provided at the optical element holding member 28 is tilted upward.

According to such a configuration, in the endoscope 1, when the operation lever 8 provided at the operation portion 3 is tilted forward (in the direction of the arrow U in the drawing) from the initial position, the direction of view with respect to the subject is changed upward (UP).

On the other hand, as shown in FIG. 20, in the endoscope 1, when the operation lever 8 is tilted backward (in the direction of the arrow D in the drawing) from the initial position, the operation rod 8a is tilted backward around the rotary shaft 42, to thereby cause the tilt rod 45, which has the spherical portion 45a engageably inserted in the cylindrical hole 41a of the columnar portion 41 provided on the operation rod 8a, to be tilted forward around the shaft 23. As a result, the transmission rod 24 moves backward.

Then, the backward movement of the transmission rod 24 causes the optical element holding member 28, not shown here, to be pulled backward, and thereby the optical element holding member 28 is rotationally moved downward. As a result, the trapezoidal prism 29 provided at the optical element holding member 28 is tilted downward.

According to such a configuration, in the endoscope 1, when the operation lever 8 provided at the operation portion 3 is tilted backward (in the direction of the arrow D in the drawing) from the initial position, the direction of view with respect to the subject is changed downward (DOWN).

Thus, the direction of view of the endoscope 1 can be changed upward and downward by the forward and backward tilting operations of the operation lever 8 provided at the operation portion 3.

In addition, as shown in FIG. 21, in the endoscope 1, when the operation lever 8 provided at the operation portion 3 is tilted leftward (in the direction of the arrow L in the drawing) from the initial position, the operation rod 8a is tilted leftward around the rotary shaft pin 44 provided at the ring member 43, to thereby cause the tilt rod 45, which has the spherical portion 45a engageably inserted in the cylindrical hole 41a of the columnar portion 41 provided on the operation rod 8a, to be tilted rightward around the shaft 23.

At this time, the rotational force is applied to the large-diameter cylinder portion 12c through the shaft 23 fixed to the shaft receiving portion 8b to which the tilt rod 45 is connected, to cause the rotary cylinder 12 to move rotationally rightward around the central axis X in the operation portion casing 14 of the operation portion 3 and the exterior tube 11.

As a result, the optical element holding member 28 provided at the distal end part of the insertion portion 2 to move rotationally in the clockwise direction, to cause the trapezoidal prism 29 provided at the optical element holding member 28 to be tilted leftward.

According to such a configuration, when the operation lever 8 provided at the operation portion 3 is tilted leftward (in the direction of the arrow L in the drawing) from the initial position, the direction of view of the endoscope 1 is changed leftward which is the direction same as the operation direction of the operation lever.

In addition, as shown in FIG. 22, in the endoscope 1, when the operation lever 8 provided at the operation portion 3 is tilted rightward (in the direction of the arrow R) from the initial position, the operation rod 8a is tilted rightward around the rotary shaft pin 44 provided at the ring member 43, to thereby cause the tilt rod 45, which has the spherical portion 45a engageably inserted in the cylindrical hole 41a of the columnar portion 41 provided on the operation rod 8a, to be tilted leftward around the shaft 23.

At this time, the rotational force is applied to the large-diameter cylinder portion 12c through the shaft 23 fixed to the shaft receiving portion 8b to which the tilt rod 45, which, together with the rotary cylinder 12, configures a second transmission member in the present embodiment, is connected, to thereby cause the rotary cylinder 12 to move rotationally leftward around the central axis X in the operation portion casing 14 of the operation portion 3 and the exterior tube 11.

Therefore, the optical element holding member 28 provided at the distal end part of the insertion portion 2 is moved rotationally in the counterclockwise direction, to thereby cause the trapezoidal prism 29 provided at the optical element holding member 28 to be tilted rightward.

According to such a configuration, when the operation lever 8 provided at the operation portion 3 is tilted rightward (in the direction of the arrow R in the drawing) from the initial position, the direction of view of the endoscope 1 is changed rightward (Right) which is the direction same as the operation direction of the operation lever.

Thus, the direction of view of the endoscope 1 can be changed leftward and rightward which are the same directions as the leftward and rightward tilting operation directions of the operation lever 8 provided at the operation portion 3.

Therefore, also the endoscope 1 according to the present embodiment is capable of changing the direction of view upward, downward, leftward and rightward by the forward, backward, leftward, and rightward tilting operations of the operation lever 8 provided at the operation portion 3, similarly as the endoscope 1 according to the first embodiment.

Note that the endoscope 1 is configured such that, in the operation direction of the operation lever 8, the forward tilting operation causes the direction of view to be changed upward, the backward tilting operation causes the direction of view to be changed downward, the leftward tilting operation causes the direction of view to be changed leftward, and the rightward tilting operation causes the direction of view to be changed rightward.

Therefore, also the endoscope 1 according to the present embodiment has the effects same as those in the first embodiment, and can be geared to the operation direction of the operation lever 8 in accordance with the preference of the user which is different from that in the first embodiment.

Note that if the configurations in the various kinds of modified examples recited in the first embodiment can be applied to the endoscope 1 according to the present embodiment, the endoscope 1 may be modified to the configurations.

Third Embodiment

Next, an endoscope according to the third embodiment of the present invention will be described with reference to drawings.

Note that, also in the description below, the constituent elements same as those in the first embodiment are attached with the same reference numerals, and detailed descriptions thereof will be omitted.

Figure 23:
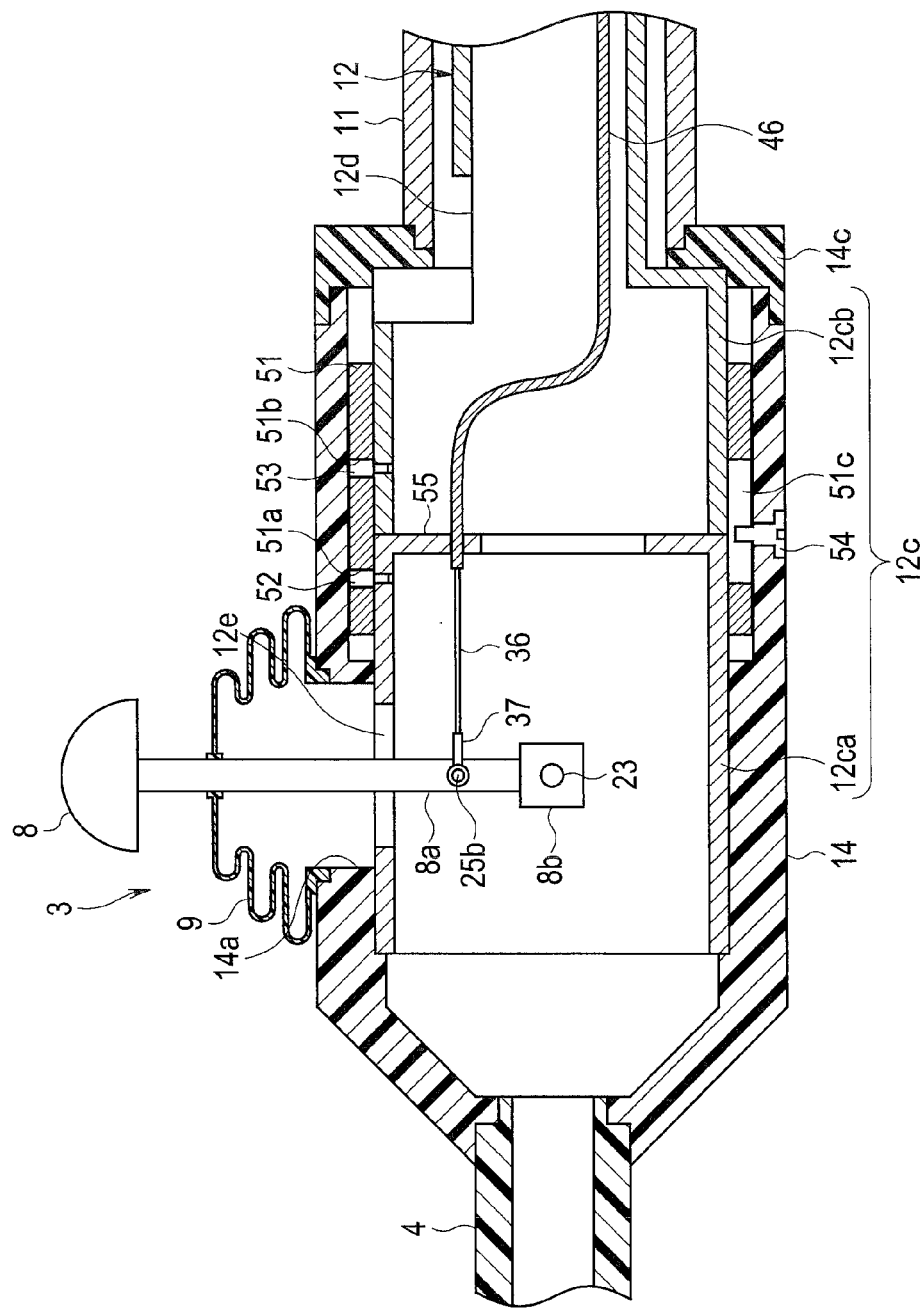
FIG. 23 is a cross-sectional view showing a configuration of an operation portion of an endoscope according to a third embodiment.
Figure 24:
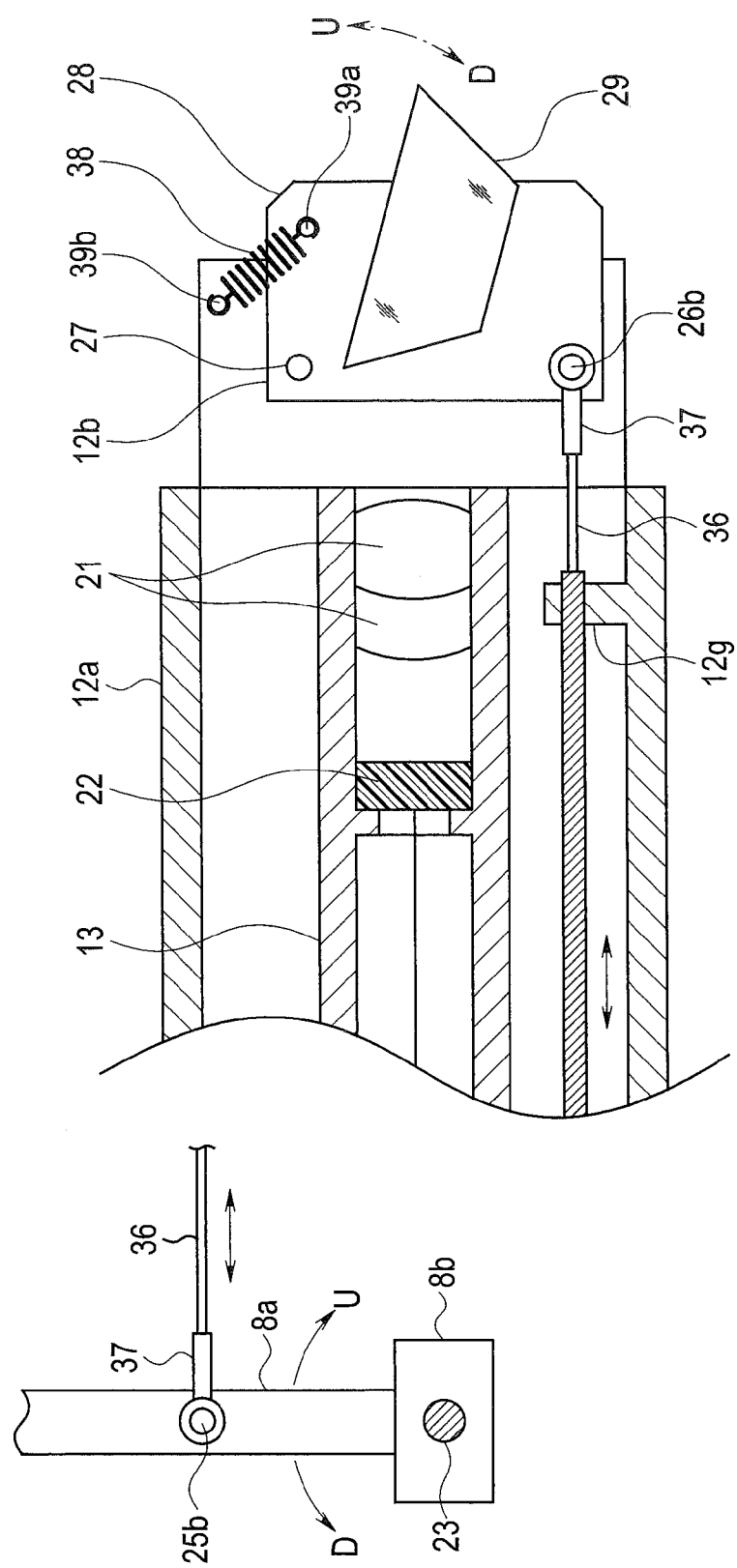
FIG. 24 schematically shows a configuration for rotationally moving an optical element holding member provided with a trapezoidal prism by a wire according to the third embodiment.
Figure 25:
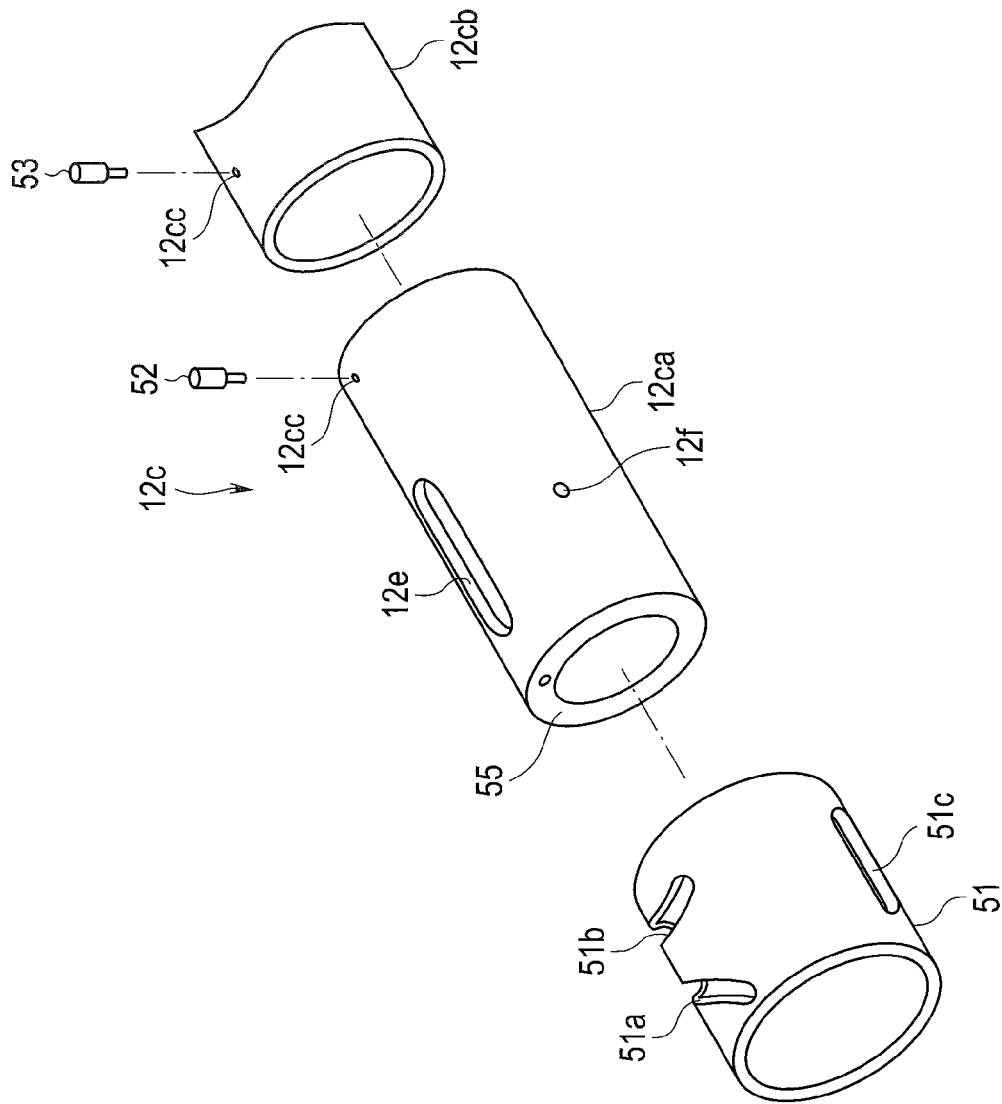
FIG. 25 is an exploded perspective view showing configurations of a first large-diameter cylinder portion, a second large-diameter cylinder portion, and a slide cylinder of a rotary cylinder according to the third embodiment.
Figure 26:
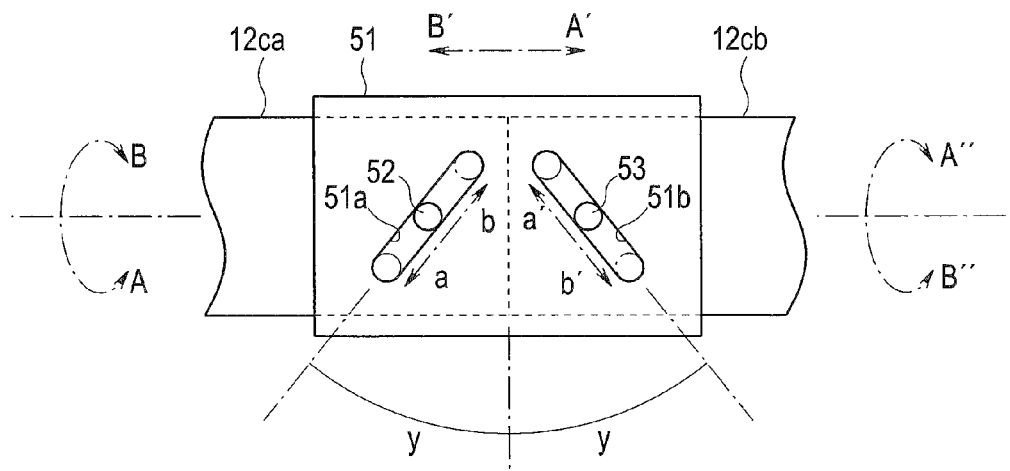
FIG. 26 is a top view for illustrating movements of the first large-diameter cylinder portion, the second large-diameter cylinder portion, and the slide cylinder of the rotary cylinder according to the third embodiment.
Figure 27:
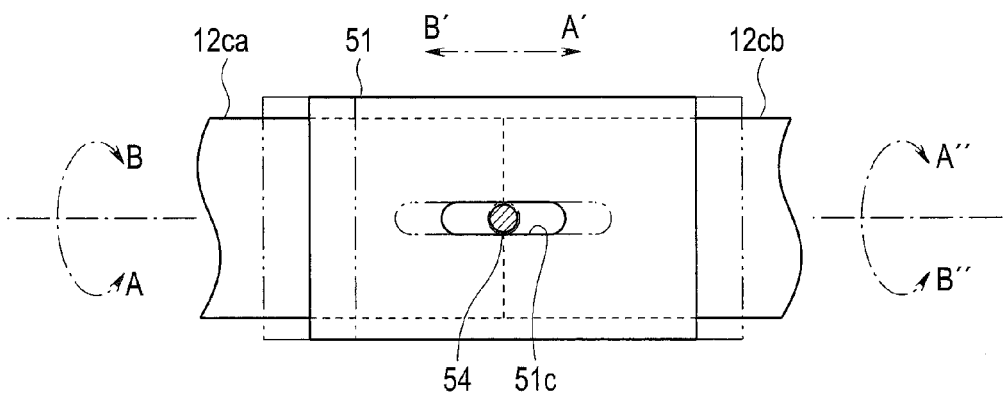
FIG. 27 is a bottom view for illustrating the movements of the first large-diameter cylinder portion, the second large-diameter cylinder portion, and the slide cylinder of the rotary cylinder according to the third embodiment.

FIG. 23 is a cross-sectional view showing the configuration of the operation portion of the endoscope, FIG. 24 schematically shows the configuration for rotationally moving the optical element holding member provided with the trapezoidal prism by the wire, FIG. 25 is an exploded perspective view showing configurations of a first large-diameter cylinder portion, a second large-diameter cylinder portion, and a slide cylinder of a rotary cylinder, FIG. 26 is a top view for illustrating movements of the first large-diameter cylinder portion, the second large-diameter cylinder portion, and the slide cylinder of the rotary cylinder, and FIG. 27 is a bottom view for illustrating the movements of the first large-diameter cylinder portion, the second large-diameter cylinder portion, and the slide cylinder of the rotary cylinder.

As shown in FIG. 23, the endoscope 1 according to the present embodiment includes a wire 36 as the transmission member for rotationally moving the optical element holding member 28 provided with the trapezoidal prism by the tilting operation of the operation lever 8 provided at the operation portion 3. Note that the configuration of the endoscope 1 using the wire 36 is similar to that in the fourth modified example in the first embodiment. Therefore, only different points will be described.

In the endoscope 1, the large-diameter cylinder portion 12c of the rotary cylinder 12 provided so as to be rotationally movable in the operation portion 3 and the insertion portion 2 includes two cylindrical portions, i.e., a first large-diameter cylinder portion 12ca which serves as a fourth shaft in the present embodiment and a second large-diameter cylinder portion 12cb which serves as a third shaft in the present embodiment.

In addition, the endoscope 1 is provided with a slide cylinder 51 on the outer circumference of the first large-diameter cylinder portion 12ca and the second large-diameter cylinder portion 12cb in order to control the direction in which the rotary cylinder 12 moves rotationally by the tilting operation of the operation lever 8 provided at the operation portion 3. Note that detailed configuration of the rotary cylinder 12 will be described later.

The wire 36 which serves as a first transmission member in the present embodiment is inserted in a wire guard 46 which is a coil tube. The wire guard 46 has the proximal end which is penetrated through the upper side of an inward flange 55 protruding in the inner diameter direction at the distal end of the first large-diameter cylinder portion 12ca, and fixed and held at the inward flange.

The distal end of the wire guard 46 is penetrated through a holding portion 12g which protrudes in the inner diameter direction at the distal end part of the small-diameter cylinder portion 12a, and fixed and held at the holding portion, as shown in FIG. 24.

The wire 36 is configured such that the wire clamp 37 provided at the proximal end portion of the wire is connected, so as to be rotationally movable, to the halfway part of the operation rod 8a of the operation lever 8, by the pin 25b, the halfway part being located on the upper side with respect to the shaft receiving portion 8b on the operation rod 8a. Note that other configurations of the transmission mechanism for rotationally moving the optical element holding member 28 provided with the trapezoidal prism are the same as those in the fourth modified example of the first embodiment.

In the endoscope 1 according to the present embodiment, when the operation lever 8 provided at the operation portion 3 is tilted forward (in the direction of the arrow U in FIG. 24) from the initial position, the wire 36 is relaxed, to thereby cause the optical element holding member 28 to rotationally move upward around the rotary shaft 27 with a tensile force of the tension spring 38.

On the other hand, in the endoscope 1, when the operation lever 8 provided at the operation portion 3 is tilted backward (in the direction of the arrow D in FIG. 24) from the initial position, the wire 36 is pulled, to thereby cause the optical element holding member 28 to rotationally move downward around the rotary shaft 27 against the tensile force of the tension spring 38.

Therefore, according to the endoscope 1 of the present embodiment, the optical element holding member 28 provided with the trapezoidal prism 29 is rotationally moved by the forward or backward tilting operation of the operation lever 8 in the direction opposite to the direction recited in the fourth modified example of the first embodiment. Accordingly, the forward and backward tilting operation directions of the operation lever 8 when changing the direction of view upward and downward are opposite to the tilting operation directions in the fourth modified example.

In addition, the large-diameter cylinder portion 12c of the rotary cylinder 12 includes the first large-diameter cylinder portion 12ca and the second large-diameter cylinder portion 12cb, as shown in FIGS. 23 and 25. Note that FIG. 23 does not show the image pickup system holding cylinder 13.

At the top portion of the outer circumference of the proximal end part of the first large-diameter cylinder portion 12ca, a hole portion 12cc to which a first cam pin 52 is secured is formed, and similarly at the top portion of the outer circumference of the distal end part of the second large-diameter cylinder portion 12cb, a hole portion 12cc to which a second cam pin 53 is secured is formed.

Note that a long hole 12e and a shaft holding hole 12f of the rotary cylinder 12 are formed on the first large-diameter cylinder portion. In addition, the second large-diameter cylinder portion 12cb includes a cutout portion 12d, and the small-diameter cylinder portion 12a is provided continuously with the distal end side of the second large-diameter cylinder portion 12cb.

The slide cylinder 51 is a cylinder body having on the upper side thereof a first cam groove 51a and a second cam groove 51b, which are linear cam grooves, and having on the lower side thereof a third cam groove 51c which is a linear cam groove.

The first cam groove 51a and the second cam groove 51b are formed in a chevron shape such that each of the first and second cam grooves has a predetermined angle y with respect to the transverse direction of the slide cylinder 51, as shown in FIG. 26.

The slide cylinder 51 is configured to allow the first large-diameter cylinder portion 12ca and the second large-diameter cylinder portion 12cb to be inserted therethrough, and the first and second large-diameter cylinder portions are fixed to the slide cylinder such that the first cam pin 52 or the second cam pin 53 enters into the first cam groove 51a or the second cam groove 51b.

Note that, on the lower portion of the operation portion casing 14 of the operation portion 3, a third cam pin 54 which is screwed from the outer circumferential portion side of the operation portion casing and enters into the third cam groove 51c of the slide cylinder 51 (see FIGS. 23 and 27). In addition, the operation portion casing 14 includes a cover casing 14c to which the exterior tube 11 of the insertion portion 2 is connected, in such a manner that the cover casing 14c closes the opening at the distal end of the operation portion casing 14.

In the endoscope 1 according to the present embodiment as described above, when the operation lever 8 provided at the operation portion 3 is tilted leftward or rightward direction from the initial position, the first large-diameter cylinder portion 12ca is moved rotationally in one of the leftward and rightward directions, the slide cylinder 51 moves forward or backward, and the second large-diameter cylinder portion 12cb is moved rotationally in the other of the leftward and rightward directions.

In detail, when the first large-diameter cylinder portion 12ca moves rotationally in the A direction, the first cam pin 52 moves in the "a" direction, as shown in FIGS. 26 and 27. At this time, in accordance with the movement of the first cam pin 52 in the "a" direction, the slide cylinder 51 moves in the A' direction along the first cam groove 51a into which the first cam pin 52 enters, that is, moves forward.

The slide cylinder 51 is rectilinearly guided, by the third cam pin 54 which enters into the third cam groove 51c, without being moved rotationally.

When the slide cylinder 51 moves in the A' direction which is forward direction, a force for causing the second cam pin 53 which enters into the second cam groove 51b to move in the a' direction along the second cam groove 51b works, to thereby cause the second large-diameter cylinder portion 12cb to move rotationally in the A" direction which is opposite to the A direction in which the first large-diameter cylinder portion 12ca moves rotationally.

When the first large-diameter cylinder portion 12ca moves rotationally in the B direction, the first cam pin 52 moves in the b direction. At this time, the slide cylinder 51 moves in the B' direction, that is, backward direction, in accordance with the movement of the first cam pin 52 in the b direction.

Also at this time, the slide cylinder 51 is rectilinearly guided by the third cam pin 54 which enters into the third cam groove 51c, without being moved rotationally.

When the slide cylinder 51 moves in the B' direction which is the backward direction, a force for causing the second cam pin 53 which enters into the second cam groove 51b to move in the b' direction along the second cam groove 51b works, to thereby cause the second large-diameter cylinder portion 12cb to move rotationally in the B" direction which is opposite to the B direction in which the first large-diameter cylinder portion 12ca moves rotationally.

Thus, the rotary cylinder 12 is configured such that the first large-diameter cylinder portion 12ca and the second large-diameter cylinder portion 12cb rotationally move in the directions opposite to each other, with the cylindrical cam mechanism constituted of the respective cam grooves 51a, 51b, and 51c of the slide cylinder 51 and the respective cam pins 52, 53, and 54.

That is, in the endoscope 1 according to the present embodiment, similarly as in the one in the second embodiment, when the operation lever 8 provided at the operation portion 3 is tilted leftward or rightward from the initial position, the rotary cylinder 12 moves rotationally in the direction opposite to the leftward or rightward tilting operation direction of the operation lever 8. Therefore, it is possible to change the direction of view leftward or rightward which is same as the leftward or rightward tilting operation direction of the operation lever 8.

Therefore, also the endoscope 1 according to the present embodiment is capable of changing the direction of view upward, downward, leftward and rightward by the forward, backward, leftward and rightward tilting operations of the operation lever 8 provided at the operation portion 3, similarly as in the endoscope according to the first embodiment.

Note that, similarly as in the endoscope in the second embodiment, also the endoscope 1 in the present embodiment is configured such that, in the operation direction of the operation lever 8, the forward tilting operation causes the direction of view to be changed upward, the backward tilting operation causes the direction of view to be changed downward, the leftward tilting operation causes the direction of view to be changed leftward, and the rightward tilting operation causes the direction of view to be changed rightward.

Therefore, the endoscope 1 according to the present embodiment has the effects same as those in the first embodiment, and can be geared to the operation direction of the operation lever 8 in accordance with the preference of the user, which is different from that in the first embodiment.

Note that if the configurations in the various kinds of modified examples recited in the first embodiment can be applied to the endoscope 1 according to the present embodiment, the endoscope 1 may be modified to the configurations.

Fourth Embodiment

Next, an endoscope according to the fourth embodiment of the present invention will be described with reference to drawings.

Note that, also in the description below, the constituent elements same as those in the first embodiment are attached with the same reference numerals, and detailed descriptions thereof will be omitted.

Figure 28:
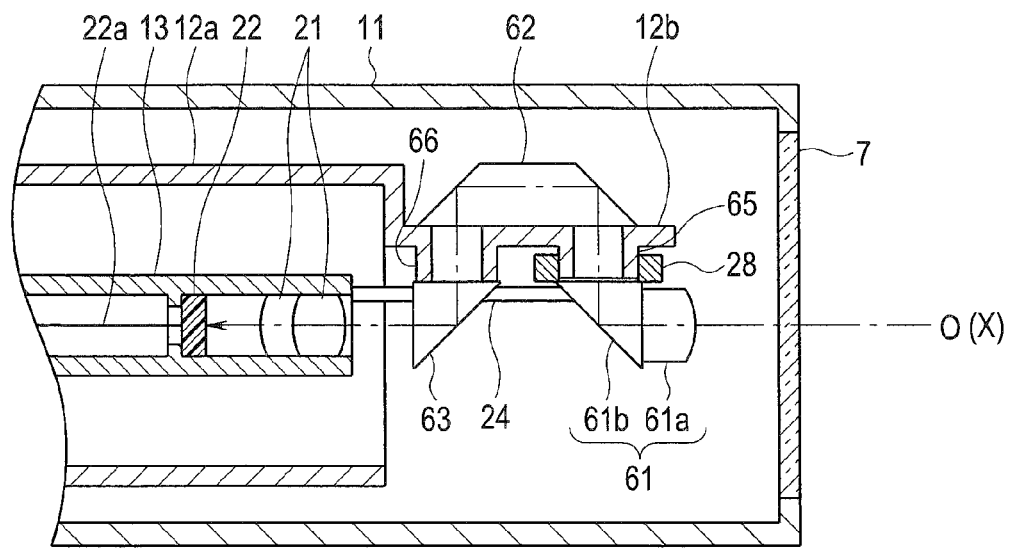
FIG. 28 is a cross-sectional view in a lateral direction showing a configuration of a distal end part of an insertion portion of an endoscope according to a fourth embodiment.
Figure 29:
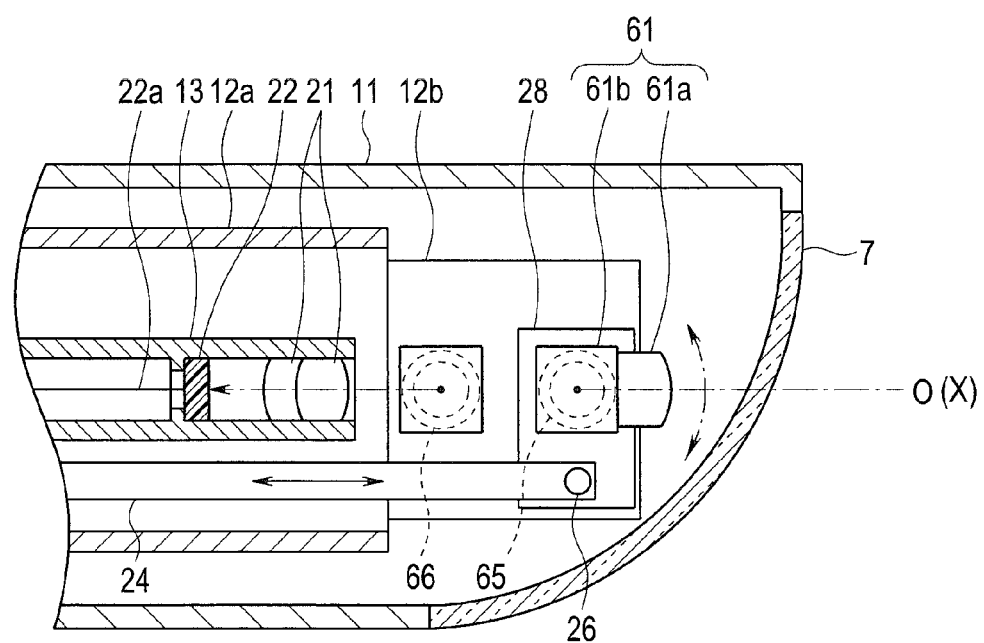
FIG. 29 is a cross-sectional view in a vertical direction showing the configuration of the distal end part of the insertion portion of the endoscope according to the fourth embodiment.

FIG. 28 is a cross-sectional view in a lateral direction showing the configuration of the distal end part of the insertion portion of the endoscope, and FIG. 29 is a cross-sectional view in a vertical direction showing the configuration of the distal end part of the insertion portion of the endoscope.

The present embodiment is different in the configuration for moving the prism as the optical element provided at the distal end part of the insertion portion 2 of the endoscope 1 to change the direction of view upward and downward.

Specifically, as shown in FIG. 28 and FIG. 29, in the endoscope 1 according to the present embodiment, a protrusion portion 12b protruded from the distal end of the small-diameter cylinder portion 12a of the rotary cylinder 12 is fainted in substantially a plane shape.

The protrusion portion 12b includes, on one surface thereof, a first cylindrical portion 65 which serves as a first shaft in the present embodiment and a second cylindrical portion 66, each of which protrudes in the direction of the central axis X and includes a hole portion, so as to juxtapose with each other in the forward/backward direction.

The optical element holding member 28 is fitted so as to be rotationally movable in the first cylindrical portion 65 of the protrusion portion 12b, by the hole portion formed on the upper portion side of the optical element holding member 28 being externally fitted to the first cylindrical portion 65.

A first prism 61 including an objective lens 61a and a triangular prism 61b in an integrated manner is fixed to the optical element holding member 28. Note that the transmission rod 24 is connected to the optical element holding member 28 through the rotary shaft member 26 so that the transmission rod 24 can move forward or backward.

The first prism 61 is fixed at the position of the hole portion of the optical element holding member 28 so as to allow the light along the photographing optical axis O, which is reflected by the triangular prism 61b, to pass through the first cylindrical portion 65. Note that the first prism 61 is disposed such that the center of the objective lens 61a is located on the central axis X.

The protrusion portion 12b includes a trapezoidal prism 62 on the other surface, that is, the surface opposite to the surface which faces the central axis X. In addition, a second prism 63 is fixed to the second cylindrical portion 66 of the protrusion portion 12b. The second prism 63 is also disposed so as to allow the light along the photographing optical axis O to pass through the second cylindrical portion 66.

Thus, the protrusion portion 12b is provided with the first prism 61, the trapezoidal prism 62 and the third prism 63, and the light along the photographing optical axis O, which is incident on the objective lens 61a of the first prism 61, is reflected by the triangular prism 61b of the first prism 61, the trapezoidal prism 62, and the second prism, to be image-formed on the image pickup device 22 through the image formation lenses 21.

In the endoscope 1 thus configured, the optical element holding member 28 moves rotationally around the center of the first cylindrical portion 65 by the transmission rod 24 that moves forward or backward by the forward or backward tilting operation of the operation lever 8 provided at the operation portion 3, to thereby cause the first prism 61 to tilt in the upward or downward direction, and the direction of view is changed upward or downward.

Note that, in the endoscope 1, the configuration for changing the direction of view in the leftward and rightward directions by the leftward and rightward tilting operations of the operation lever 8 provided at the operation portion 3 is the same as that in the above-described embodiments.

In addition, the electronic endoscope provided with the image pickup device 22 is exemplified as the endoscope 1. The endoscope 1, however, is not limited to such an endoscope, and the above-described embodiments are applicable to the endoscope having a configuration in which a relay lens is provided to transmit an image of an object.

Furthermore, if the configurations recited in the various kinds of modified examples in the first embodiment or in the second embodiment can be applied to the endoscope 1 according to the present embodiment, the endoscope 1 may be modified to the configurations.

The invention recited in the respective embodiments are not limited to the embodiments or the modified examples thereof, and various modifications are possible in the practical stage in a range without departing from the gist of the invention. Furthermore, the respective embodiments include inventions in various stages, and various inventions can be extracted by appropriately combining a plurality of disclosed constituent elements.

For example, even if some constituent elements are deleted from all the constituent elements shown in the respective embodiments, the configuration from which some constituent elements are deleted can be extracted as the invention if the described problem can be solved and described effects can be obtained.

What is claimed is:

1. An endoscope comprising:
a rigid insertion portion having a first axis;
an operation portion provided continuously with a proximal end of the insertion portion;
a first shaft provided at a distal end part of the insertion portion so as to be perpendicular to the first axis;
an optical element disposed so as to be rotationally movable around both the first shaft and a second axis parallel to the first axis to change a direction of view of the optical element upward, downward, leftward, and rightward;
a second shaft which is disposed at the operation portion and which is perpendicular to the second axis;
a single operation member configured to be able to swing forward, backward, leftward, and rightward around the second shaft and the second axis;
a first transmission member to which the optical element and the operation member are connected, the first transmission member being configured to transmit a rotational force around the first shaft to the optical element by a tilting operation of the operation member around the second shaft; and
a second transmission member including a distal end part at which the optical element is rotatably disposed relative to the first shaft, the second transmission member further including a proximal end part rotatably disposed relative to the operation member such that the second transmission member transmits a rotational force around the second axis to the optical element by a tilting operation of the operation member around the second axis.

2. The endoscope according to claim 1, wherein the first shaft around which the optical element is rotationally movable and the second shaft around which the operation member is tilted are parallel to each other.

3. The endoscope according to claim 1, wherein, when the operation member is tilted forward around the second shaft, the first transmission member is moved backward and the optical element is rotationally moved downward around the first shaft, to cause the direction of view of the optical element to be changed downward, and when the operation member is tilted backward around the second shaft, the first transmission member is moved forward and the optical element is rotationally moved upward around the first shaft, to cause the direction of view of the optical element to be changed upward.

4. The endoscope according to claim 1, wherein, when the operation member is tilted forward around the second shaft, the first transmission member is moved forward and the optical element is rotationally moved upward around the first shaft, to cause the direction of view of the optical element to be changed upward, and when the operation member is tilted backward around the second shaft, the first transmission member is moved backward and the optical element is rotationally moved downward around the first shaft, to cause the direction of view of the optical element to be changed downward.

5. The endoscope according to claim 1, wherein, when the operation member is tilted leftward around the second axis, the second transmission member is rotationally moved leftward and the optical element is rotationally moved leftward around a photographing optical axis, to cause the direction of view of the optical element to be changed rightward, and when the operation member is tilted rightward around the second axis, the second transmission member is rotationally moved rightward and the optical element is rotationally moved rightward around the photographing optical axis, to cause the direction of view of the optical element to be changed leftward.

6. The endoscope according to claim 1, wherein, when the operation member is tilted leftward around the second axis, the second transmission member is rotationally moved rightward and the optical element is rotationally moved rightward around a photographing optical axis, to cause the direction of view of the optical element to be changed leftward, and when the operation member is tilted rightward around the second axis, the second transmission member is rotationally moved leftward and the optical element is rotationally moved leftward around the photographing optical axis, to cause the direction of view of the optical element to be changed rightward.

7. The endoscope according to claim 1, wherein the first transmission member is a rigid transmission rod.

8. The endoscope according to claim 1, wherein the first transmission member is a transmission wire.

9. The endoscope according to claim 1, wherein the first axis and the second axis are coaxial with each other.

* * * * *